(12) United States Patent
Miller et al.

(10) Patent No.: US 12,365,656 B2
(45) Date of Patent: Jul. 22, 2025

(54) OXAZOLIDINONE COMPOUNDS AND METHODS OF USE THEREOF AS ANTIBACTERIAL AGENTS

(71) Applicant: Merck Sharp & Dohme LLC, Rahway, NJ (US)

(72) Inventors: Randall R. Miller, Lebanon, NJ (US); Joseph A. Kozlowski, Princeton, NJ (US); Philippe Nantermet, Lansdale, PA (US); David B. Olsen, Lansdale, PA (US); Jing Su, Scotch Plains, NJ (US); Lihu Yang, Edison, NJ (US); Takao Suzuki, Shanghai (CN); Brendan Crowley, Collegeville, PA (US); Negxue Wang, Shanghai (CN); Lanying You, Shanghai (CN)

(73) Assignee: Merck Sharp & Dohme LLC, Rahway, NJ (US)

( * ) Notice: Subject to any disclaimer, the term of this patent is extended or adjusted under 35 U.S.C. 154(b) by 938 days.

(21) Appl. No.: 17/422,308

(22) PCT Filed: Dec. 19, 2019

(86) PCT No.: PCT/CN2019/126641
§ 371 (c)(1),
(2) Date: Jul. 12, 2021

(87) PCT Pub. No.: WO2020/147504
PCT Pub. Date: Jul. 23, 2020

(65) Prior Publication Data
US 2022/0081403 A1    Mar. 17, 2022

Related U.S. Application Data

(60) Provisional application No. 62/793,922, filed on Jan. 18, 2019.

(51) Int. Cl.
| | |
|---|---|
| *C07D 263/06* | (2006.01) |
| *A61K 31/421* | (2006.01) |
| *A61K 31/422* | (2006.01) |
| *A61K 31/437* | (2006.01) |
| *A61K 31/4439* | (2006.01) |
| *A61K 31/498* | (2006.01) |

(Continued)

(52) U.S. Cl.
CPC .......... *C07D 263/06* (2013.01); *A61K 31/421* (2013.01); *A61K 31/422* (2013.01); *A61K 31/437* (2013.01); *A61K 31/4439* (2013.01); *A61K 31/498* (2013.01); *A61K 31/541* (2013.01); *A61K 45/06* (2013.01); *A61P 31/06* (2018.01); *C07D 413/12* (2013.01); *C07D 471/04* (2013.01); *C07D 495/04* (2013.01); *C07F 9/653* (2013.01); *C07F 9/655363* (2013.01)

(58) Field of Classification Search
CPC .. A61K 31/421; A61K 31/422; A61K 31/437; A61K 31/4439; A61K 31/498; A61K 31/541; A61K 45/06; A61P 31/00; A61P 31/06; C07D 263/06; C07D 413/12; C07D 471/04; C07D 495/04; C07F 9/653; C07F 9/655363
See application file for complete search history.

(56) References Cited

U.S. PATENT DOCUMENTS

| | | | |
|---|---|---|---|
| 4,150,029 A * | 4/1979 | Dostert | A61P 25/24 564/384 |
| 6,255,304 B1 | 7/2001 | Hester, Jr. | |

(Continued)

FOREIGN PATENT DOCUMENTS

| | | |
|---|---|---|
| CN | 1437603 A | 8/2003 |
| CN | 102131811 A | 7/2011 |

(Continued)

OTHER PUBLICATIONS

CAS Registry No. 154590-84-8, entered Registry on Apr. 26, 1994. (Year: 1994).*

(Continued)

*Primary Examiner* — Joseph K McKane
*Assistant Examiner* — Ashli Ariana Chicks
(74) *Attorney, Agent, or Firm* — James T. Corcoran; Catherine D. Fitch

(57) ABSTRACT

The present invention discloses oxazolidinone compounds of Formula (I): (I) and pharmaceutically acceptable salts thereof, wherein A and E, are as defined herein. The present invention also relates to compositions which comprise at least one oxazolidinone compound of the invention. The invention also provides methods for inhibiting growth of mycobacterial cells as well as a method of treating mycobacterial infections by *Mycobacterium tuberculosis* comprising administering a therapeutically effective amount of an oxazolidinone of the invention and/or a pharmaceutically acceptable salt thereof, or a composition comprising such compound and/or salt.

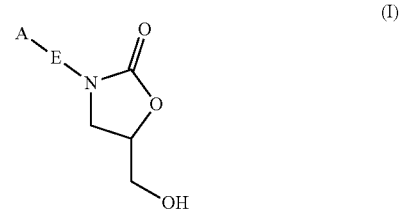

(I)

17 Claims, No Drawings

(51) Int. Cl.

| | |
|---|---|
| *A61K 31/541* | (2006.01) |
| *A61K 45/06* | (2006.01) |
| *A61P 31/06* | (2006.01) |
| *C07D 413/06* | (2006.01) |
| *C07D 413/12* | (2006.01) |
| *C07D 471/04* | (2006.01) |
| *C07D 495/04* | (2006.01) |
| *C07F 9/653* | (2006.01) |
| *C07F 9/6553* | (2006.01) |

(56) References Cited

U.S. PATENT DOCUMENTS

| | | |
|---|---|---|
| 7,141,583 B2 | 11/2006 | Gravestock et al. |
| 8,575,337 B2 | 11/2013 | Katoh et al. |
| 10,550,092 B2 | 2/2020 | Cooper et al. |
| 2003/0166620 A1 | 9/2003 | Lee et al. |
| 2003/0216373 A1 | 11/2003 | Gravestock et al. |
| 2011/0098471 A1 | 4/2011 | Katoh et al. |

FOREIGN PATENT DOCUMENTS

| | | | | |
|---|---|---|---|---|
| CN | 103360379 A | 10/2013 | | |
| CN | 108135887 A | 6/2018 | | |
| CN | 108348507 A | 7/2018 | | |
| EP | 1229033 A2 | 8/2002 | | |
| JP | 2003335762 A | 11/2003 | | |
| WO | 1996015130 A1 | 5/1996 | | |
| WO | 1997009328 A1 | 3/1997 | | |
| WO | WO-0181350 A1 | * | 11/2001 | ........... C07D 231/12 |
| WO | 2002081470 A1 | 10/2002 | | |
| WO | 2005019211 A2 | 3/2005 | | |
| WO | 2005058886 A1 | 6/2005 | | |
| WO | 2005061468 A1 | 7/2005 | | |
| WO | 2006022794 A1 | 3/2006 | | |
| WO | 2007023507 A2 | 3/2007 | | |
| WO | 2009157423 A1 | 12/2009 | | |
| WO | WO-2012033952 A1 | * | 3/2012 | ........... A61K 9/0014 |
| WO | WO-2017015106 A1 | * | 1/2017 | ........... A61K 31/422 |
| WO | 2017066964 A1 | 4/2017 | | |
| WO | WO-2017070024 A1 | * | 4/2017 | ........... A61K 31/421 |
| WO | 2017143112 A2 | 8/2017 | | |
| WO | 2018170664 A1 | 9/2018 | | |
| WO | 2018175185 A1 | 9/2018 | | |

OTHER PUBLICATIONS

Ramsay, R.R. et al., Monoamine Oxidases: to Inhibit or Not to Inhibit, Mini Reviews in Medicinal Chemistry, 2003, 129-136, 3.

Balasubramanian, V. et al., Bactericidal Activity and Mechanism of Action of AZD5847, a Novel Oxazolidinone for Treatment of *Tuberculosis*, Antimicrobial Agents and Chemotherapy, 2014, 495-502, 58.

Flanagan, Shawn, et al., Nonclinical and Pharmacokinetic Assessments to Evaluate the Potential of Tedizolid and Linezolid To Affect Mitochondrial Function, Antimicrobial Agents and Chemotherapy, 2015, p. 178-185, vol. 59, No. 1.

Hickey et al., Experimental model of reversible myelosuppression caused by short-term, high-dose oxazolidinone administration, Therapy, 2006, 521-526, 3(4).

Lee, Myungsun, Linezolid for Treatment of Chronic Extensively Drug-Resistant Tuberculosis, The New England Journal of Medicine, 2012, p. 1508-1518, vol. 367, No. 16.

Pandit, N. et al., Current Updates on Oxazolidinone and its Significance, International Journal of Medicinal Chemistry, 2012, 1-24, N/A.

Shaw et al., The oxazolidinones: past, present, and future, Ann. N.Y. Acad. Sci., 2011, 48-70, 1241.

Suzuki, Hideyuki, et al., Potent Oxazolidinone Antibacterials with Heteroaromatic C-Ring Substructure, ACS Medicinal Chemistry Letters, 2013, p. 1074-1078, vol. 4.

Takrouri, Khuloud et al., Progress against *Escherichia coli* with the Oxazolidinone Class of Antibacterials: Test Case for a General Approach To Improving Whole-Cell Gram-Negative Activity, ACS Infect. Dis., 2016, 405-426, 2.

Yang et al., Discovery of a Teraryl Oxazolidinone Compound (S)-N-((3-(3-Fluoro-4-(4-(pyridin-2-yl)-1H-pyrazol-1-yl) phenyl)-2-oxooxazolidin-5-yl)-methyl)acetamide Phosphate as a Novel Antimicrobial Agent with Enhanced Safety Profile and Efficacies, Journal of Medicinal Chemistry, 2015, 6389-6409, 58.

Siddiqui, Asher M. et al., Design, synthesis and biological evaluation of spiropyrimidinetriones oxazolidinone derivatives as antibacterial agents, Bioorganic & Medicinal Chemistry Letters, 2018, 1198-1206, 28.

Spaulding, Andrew et al., Compound design guidelines for evading the efflux and permeation barriers of *Escherichia coli* with the oxazolidinone class of antibacterials: Test case for a general approach to improving whole cell Gram-negative activity, Bioorganic & Medicinal Chemistry Letters, 2017, 5310-5321, 27.

\* cited by examiner

OXAZOLIDINONE COMPOUNDS AND METHODS OF USE THEREOF AS ANTIBACTERIAL AGENTS

CROSS-REFERENCE TO RELATED APPLICATIONS

This application is a National Stage application of International Patent Application No. PCT/CN19/126641, filed Dec. 19, 2019, which published as WO2020/147504 A1 on Jul. 23, 2020, and claims priority to U.S. Provisional Patent application No. 62/793,922, filed Jan. 18, 2019.

FIELD OF THE INVENTION

The present invention relates to novel oxazolidinone compounds useful for the treatment of bacterial infections, particularly mycobacterial infections. The invention also relates to methods of use of oxazolidinone compounds for the treatment of mycobacterial infections such as those caused by Mycobacteria tuberculosis.

BACKGROUND OF THE INVENTION

*Mycobacterium* is a genus of bacterium, neither truly gram-positive nor truly gram-negative, including pathogens responsible for tuberculosis (*M. tuberculosis*) and leprosy (*M. leprae*). Tuberculosis (TB), in particular, despite the availability of anti-TB drugs such as isoniazide and rifampin, is considered to be one of the worlds deadliest diseases. According to World Health Organization, in 2012, there were 8.6 million new TB cases and 1.3 million TB deaths. See, Global tuberculosis report 2013 published by the World Health Organization. Complicating the TB epidemic is the rising tide of multi-drug-resistant strains, and the deadly association with HIV. People who are HIV-positive and infected with TB are 30 times more likely to develop active TB than people who are HIV-negative, and TB is responsible for the death of one out of every three people with HIV/AIDS worldwide. See, e.g., Kaufmann et al., *Trends Microbiol.* 1: 2-5 (1993) and Bloom et al., *N. Engl. J. Med.* 338: 677-678 (1998).

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to 1010 acid-fast bacilli per gram of tissue), and consequently, the prognosis for the infected AIDS patient is poor.

Oxazolidinones are a class of compounds containing 2-oxazolidone, a 5-membered ring containing nitrogen and oxygen, which are used as antimicrobials. See, e.g. WO 2009157423. In general, oxazolidinones are known to be monoamine oxidase inhibitors and to have activity against gram-positive microorganisms. WO 2006022794, Suzuki et al., *Med. Chem. Lett.* 4:1074-1078 (2013), Yang et al., J. Med. Chem. 58:6389-6409 (2015), Shaw et al., Ann. N.Y. Acad. Sci. 1241:48-70 (2011), Several oxazolidinone antibiotics have been approved or are in clinical trials for the treatment of gram-positive bacterial infections such as methicillin resistant *Staphylococcus aureus*. Examples of oxazolidinone antibiotics include linezolid (Zyvox™, Pfizer Inc., New York, N.Y.) and tedizolid (Sivextro™, Merck Sharp & Dohme Corp., Kenilworth, NJ). Tedizolid is used to treat acute bacterial skin and skin structure infections caused by specific susceptible gram-positive bacteria. Linezolid is indicated for the treatment of several infections caused by susceptible strains of gram-positive microorganisms including nosocomial pneumonia, complicated skin and skin structure infections, and community-acquired pneumonia. In addition, it is currently being tested for the treatment of multi-drug resistant (MDR) and extensively drug-resistant (XDR) *Mycobacterium tuberculosis* (Mtb) in clinical trials. Lee et al., *N. Engl. J. Med* 367: 1508-18 (2012). Despite clinical efficacy in treating these diseases, long-term use of linezolid has been associated with adverse events including myelosuppression (including anemia and leukopenia) (Hickey et al., Therapy 3(4):521-526 (2006), neuropathy, and serotonin syndrome. These adverse events are hypothesized to be associated with the inhibition of mitochondrial protein synthesis. Flanagan et al., *Antimicrobial Agents and Chemotherapy* 59(1):178-185 (2015).

Development of oxazolidinone antibiotics that are safer than approved oxazolidinones yet at least as effective would greatly benefit Mtb patients.

SUMMARY OF THE INVENTION

The present invention is directed to certain novel oxazolidinone compounds which have antibacterial activity. The compounds, and their pharmaceutically acceptable salts, can be useful, for example, for the treatment of bacterial infections, for example, mycobacterial infections.

The present invention is direct to compounds of Formula I, or pharmaceutically acceptable salts thereof:

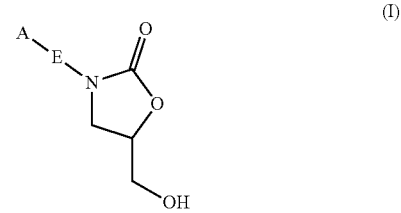

(I)

or a pharmaceutically acceptable salt thereof,
wherein:
E is a 6-membered aryl or a 5- or 6-membered heteroaryl containing from one to three heteroatoms independently selected from S, O, and N, wherein said aryl and said heteroaryl are optionally substituted with up to four substituents, which are independently selected from halogen, —CN, —CF$_3$, —CHF$_2$, —CH$_2$NH$_2$, —CH$_2$NHCOCH$_3$, —OCF$_3$, —OCHF$_2$, —OH, —O—(C$_1$-C$_6$)alkyl, C$_1$-C$_6$ alkyl, and C$_3$-C$_6$ cycloalkyl;
A is a heterocycle optionally substituted with up to four R$^8$, or an aryl optionally substituted with up to four R$^8$;
each occurrence of R$^8$ is independently selected from H, halogen, C$_1$-C$_6$ alkyl, C$_3$-C$_6$ cycloalkyl, C$_3$-C$_6$ heterocycloalkyl, —OC$_1$-C$_6$ alkyl, benzyl, —OCF$_3$, —OCHF$_2$, —OR$^3$, =O, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, —CO(R$^2$)$_2$ and —C(R$^9$)$_2$N(R$^2$)$_2$, wherein said C$_1$-C$_6$ alkyl, C$_3$-C$_6$ cycloalkyl, C$_3$-C$_6$ heterocycloalkyl, —OC$_1$-C$_6$ alkyl, and benzyl are optionally substituted with up to four F, —OCH$_3$, —OH, =O, NH$_2$, NHCH$_3$, SO$_2$R$^3$, and N(CH$_3$)$_2$;
each occurrence of R$^2$ is independently selected from H, C$_1$-C$_6$ alkyl, C$_2$-C$_6$ alkenyl, and C$_3$-C$_6$ cycloalkyl, wherein said $C_1$-$C_6$ alkyl, said $C_2$-$C_6$ alkenyl, and said $C_3$-$C_6$ cycloalkyl can be optionally substituted with up to four substituents, which are independently selected from halogen, —$OCH_3$, —OH, —$NH_2$, —$NHCH_3$, and —$N(CH_3)_2$;

$R^3$ is H, $C_1$-$C_6$ alkyl, $C_2$-$C_6$ alkenyl, $C_3$-$C_6$ heterocycloalkyl and $C_3$-$C_6$ cycloalkyl, wherein said $C_1$-$C_6$ alkyl, said $C_2$-$C_6$ alkenyl, said $C_3$-$C_6$ heterocycloalkyl and said $C_3$-$C_6$ cycloalkyl can be optionally substituted with up to four substituents, which are independently selected from halogen, methyl, —$OCH_3$, —OH, —$NH_2$, —$NHCH_3$, and —$N(CH_3)_2$; and each occurrence of $R^9$ is independently selected from H, $C_1$-$C_6$ alkyl, and $C_3$-$C_6$ cycloalkyl.

More particularly, the present invention includes compounds of Formula I, or pharmaceutically acceptable salts thereof:

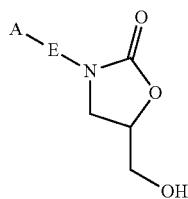

(I)

wherein:
E is a 6-membered aryl or a 5- or 6-membered heteroaryl containing from one to three heteroatoms independently selected from S, O, and N, wherein said aryl and said heteroaryl are optionally substituted with up to four substituents, which are independently selected from halogen, —CN, —$CF_3$, —$CHF_2$, —$CH_2NH_2$, —$CH_2NHCOCH_3$, —$OCF_3$, —$OCHF_2$, —OH, —O—($C_1$-$C_6$)alkyl, $C_1$-$C_6$ alkyl, and $C_3$-$C_6$ cycloalkyl;

A is a heterocycle substituted or optionally substituted with up to four $R^8$, or an aryl substituted with up to four $R^8$;

each occurrence of $R^8$ is independently selected from H, halogen, $C_1$-$C_6$ alkyl, $C_3$-$C_6$ cycloalkyl, $C_3$-$C_6$ heterocycloalkyl, benzyl, —$OCF_3$, —$OCHF_2$, —$OR^3$, =O, —CN, —$NO_2$, —$SR^3$, —$SF_5$, —$SCF_3$, —$SOR^3$, —$SO_2R^3$, —S(=O)(=N)$R^2$, —$N(R^2)_2$, —$NR^2COR^3$, —$SO_2N(R^2)_2$, —$NR^2SO_2R^3$, —COOH, —$COR^9$, —$COOR^3$, —$CON(R^2)_2$, —$CO(R^2)_2$ and —$C(R^9)_2N(R^2)_2$, wherein said $C_1$-$C_6$ alkyl, $C_3$-$C_6$ cycloalkyl, $C_3$-$C_6$ heterocycloalkyl, and benzyl are optionally substituted with up to four F, —$OCH_3$, —OH, =O, $NH_2$, $NHCH_3$, and $N(CH_3)_2$; and each occurrence of $R^2$ is independently selected from H, $C_1$-$C_6$ alkyl, $C_2$-$C_6$ alkenyl, and $C_3$-$C_6$ cycloalkyl, wherein said $C_1$-$C_6$ alkyl, said $C_2$-$C_6$ alkenyl, and said $C_3$-$C_6$ cycloalkyl can be optionally substituted with up to four substituents, which are independently selected from halogen, —$OCH_3$, —OH, $NH_2$, $NHCH_3$, and $N(CH_3)_2$;

$R^3$ is H, $C_1$-$C_6$ alkyl, $C_2$-$C_6$ alkenyl, and $C_3$-$C_6$ cycloalkyl, wherein said $C_1$-$C_6$ alkyl, said $C_2$-$C_6$ alkenyl and said $C_3$-$C_6$ cycloalkyl can be optionally substituted with up to four substituents, which are independently selected from halogen, —$OCH_3$, —OH, $NH_2$, $NHCH_3$, and $N(CH_3)_2$;

each occurrence of $R^9$ is independently selected from H, $C_1$-$C_6$ alkyl, $N(R^2)_2$ and $C_3$-$C_6$ cycloalkyl.

Also described herein are prodrugs of the compounds of Formula I, represented by the formula of Formula II:

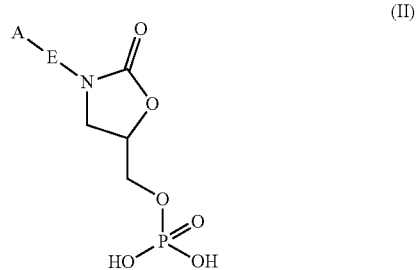

(II)

wherein:
E is a 6-membered aryl or a 5- or 6-membered heteroaryl containing from one to three heteroatoms independently selected from S, O, and N, wherein said aryl and said heteroaryl are optionally substituted with up to four substituents, which are independently selected from halogen, —CN, —$CF_3$, —$CHF_2$, —$CH_2NH_2$, —$CH_2NHCOCH_3$, —$OCF_3$, —$OCHF_2$, —OH, —O—($C_1$-$C_6$)alkyl, $C_1$-$C_6$ alkyl, and $C_3$-$C_6$ cycloalkyl;

A is a heterocycle optionally substituted with up to four $R^8$, or an aryl optionally substituted with up to four $R^8$;

each occurrence of $R^8$ is independently selected from H, halogen, $C_1$-$C_6$ alkyl, $C_3$-$C_6$ cycloalkyl, $C_3$-$C_6$ heterocycloalkyl, —$OC_1$-$C_6$ alkyl, benzyl, —$OCF_3$, —$OCHF_2$, —$OR^3$, =O, —CN, —$NO_2$, —$SR^3$, —$SF_5$, —$SCF_3$, —$SOR^3$, —$SO_2R^3$, —S(=O)(=N)$R^2$, —$N(R^2)_2$, —$NR^2COR^3$, —$SO_2N(R^2)_2$, —$NR^2SO_2R^3$, —COOH, —$COR^9$, —$COOR^3$, —$CON(R^2)_2$, —CO($R^2)_2$ and —$C(R^9)_2N(R^2)_2$, wherein said $C_1$-$C_6$ alkyl, $C_3$-$C_6$ cycloalkyl, $C_3$-$C_6$ heterocycloalkyl, —$OC_1$-$C_6$ alkyl, and benzyl are optionally substituted with up to four F, —$OCH_3$, —OH, =O, $NH_2$, $NHCH_3$, $SO_2R^3$, and $N(CH_3)_2$;

each occurrence of $R^2$ is independently selected from H, $C_1$-$C_6$ alkyl, $C_2$-$C_6$ alkenyl, and $C_3$-$C_6$ cycloalkyl, wherein said $C_1$-$C_6$ alkyl, said $C_2$-$C_6$ alkenyl, and said $C_3$-$C_6$ cycloalkyl can be optionally substituted with up to four substituents, which are independently selected from halogen, —$OCH_3$, —OH, —$NH_2$, —$NHCH_3$, and —$N(CH_3)_2$;

$R^3$ is H, $C_1$-$C_6$ alkyl, $C_2$-$C_6$ alkenyl, $C_3$-$C_6$ heterocycloalkyl and $C_3$-$C_6$ cycloalkyl, wherein said $C_1$-$C_6$ alkyl, said $C_2$-$C_6$ alkenyl, said $C_3$-$C_6$ heterocycloalkyl and said $C_3$-$C_6$ cycloalkyl can be optionally substituted with up to four substituents, which are independently selected from halogen, methyl, —$OCH_3$, —OH, —$NH_2$, —$NHCH_3$, and —$N(CH_3)_2$; and each occurrence of $R^9$ is independently selected from H, $C_1$-$C_6$ alkyl, and $C_3$-$C_6$ cycloalkyl.

The present invention also relates to a pharmaceutical composition for treating a bacterial infection in a subject, particularly an *M. tuberculosis* infection, comprising an oxazolidinone compound of the invention and a pharmaceutically acceptable carrier, diluent or excipient.

The Compounds of Formula I and pharmaceutically acceptable salts and prodrugs thereof (also referred to herein as the "Oxazolidinone Compounds") can be useful, for example, for inhibiting the growth of *Mycobacterium tuberculosis*, and/or for treating or preventing tuberculosis in a patient. Without being bound by any specific theory, it is believed that uses of the Oxazolidinone Compounds of the invention for the treatment of tuberculosis are likely to cause less myelosuppression than known oxazolidinone compounds such as linezolid because they are not associated with a high degree of inhibition of mitochondrial protein synthesis (see Examples).

The present invention is also directed to 1) methods of treating tuberculosis in a subject in need of treatment thereof, comprising administering to the subject an effective amount of an Oxazolidinone Compound; and 2) uses of an Oxazolidinone Compound for the treatment of tuberculosis.

Embodiments, sub-embodiments and features of the present invention are either further described herein or will be apparent from the ensuing description, examples and appended claims.

DETAILED DESCRIPTION OF THE INVENTION

Oxazolidinones were originally developed for use in treating gram-positive bacterial infections, particularly, methicillin-resistant *S. aureus* infections. As shown in the Examples, in vitro testing of the oxazolidinone compounds of Formula I revealed such compounds had excellent potency in inhibiting the growth of Mycobacteria tuberculosis. Additionally, Oxazolidinone Compounds of the invention are not associated with a high degree of mitochondrial protein synthesis inhibition. Thus, compounds of Formula I and their pharmaceutically acceptable salts and prodrugs are expected to be useful for the treatment of mycobacterial tuberculosis (Mtb), yet not lead to the side effects such as myelosuppression that are associated with the oxazolidinone linezolid, which is approved for treatment of Gram-positive infections. Therefore, such compounds would have significant advantages over linezolid and analogs as Mtb therapeutic agents.

The Compounds of Formula (I)

In one aspect, the present invention includes compounds of Formula I:

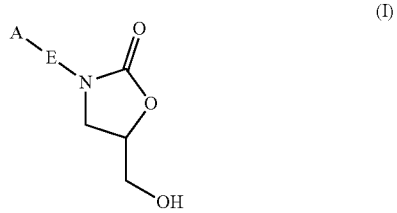

(I)

and pharmaceutically acceptable salts thereof, wherein A and E are defined above for the Compounds of Formula (I); wherein the compounds may be suitable for use for the treatment of bacterial infections, particularly mycobacterial infections.

A first embodiment of the invention (Embodiment E1) is a compound of Formula I, or a pharmaceutically acceptable salt thereof, wherein A is an aryl optionally substituted with up to four $R^8$; and wherein all other variables are as originally defined (i.e. as defined in Formula I in the Summary of the Invention.

In a sub-embodiment of Embodiment E1, A is a 6-membered aryl. In still further sub-embodiments, A is a 7-, 8-, 9-, 10-, 11-, 12-, 13-, or 14-membered aryl.

A second embodiment (Embodiment E2) is a compound of Formula I, or a pharmaceutically acceptable salt thereof, wherein, A is a heterocycle or heteroaryl, wherein from 1 to 4 of the ring atoms is independently O, N, or S and the remaining ring atoms are carbon atoms, and all other variables are as defined in the Summary of the Invention.

In a sub-embodiment of Embodiment E2, A is a 5-membered heteroaryl containing one heteroatom. In a further sub-embodiment, A is a 5-membered heteroaryl containing two heteroatoms. In another sub-embodiment A is a 5-membered heteroaryl containing three heteroatoms. In a still further sub-embodiment A is a 5-membered heteroaryl containing four heteroatoms. In another sub-embodiment, A is a 6-membered heteroaryl containing one heteroatom. In a further sub-embodiment, A is a 6-membered heteroaryl containing two heteroatoms. In another sub-embodiment A is a 6-membered heteroaryl containing three heteroatoms. In a still further sub-embodiment A is a 6-membered heteroaryl containing four heteroatoms. In still further sub-embodiments, A is a 7-, 8-, 9-, 10-, 11-, 12-, 13-, or 14-membered heteroaryl containing from one to four heteroatoms selected from N, O, and S.

In a sub-embodiment of Embodiment E2, A is a 5-membered heterocycle containing one heteroatom. In a further sub-embodiment, A is a 5-membered heterocycle containing two heteroatoms. In another sub-embodiment A is a 5-membered heterocycle containing three heteroatoms. In a still further sub-embodiment A is a 5-membered heterocycle containing four heteroatoms. In another sub-embodiment, A is a 6-membered heterocycle containing one heteroatom. In a further sub-embodiment, A is a 6-membered heterocycle containing two heteroatoms. In another sub-embodiment A is a 6-membered heterocycle containing three heteroatoms. In a still further sub-embodiment A is a 6-membered heterocycle containing four heteroatoms. In still further sub-embodiments, A is a 7-, 8-, 9-, 10-, 11-, 12-, 13-, or 14-membered heterocycle containing from one to four heteroatoms selected from N, O, and S.

A third embodiment (Embodiment E3) is a compound of Formula I, or a pharmaceutically acceptable salt thereof, wherein A is a monocyclic saturated or partially unsaturated ring optionally substituted with up to four $R^8$, wherein from 1 to 4 of the ring atoms is independently O, N, or S and the remaining ring atoms are carbon atoms, and all other variables are as defined in the Summary of the Invention.

In a sub-embodiment of Embodiment E3, A is a 5-membered monocyclic saturated or partially unsaturated ring containing one heteroatom. In a further sub-embodiment, A is a 5-membered monocyclic saturated or partially unsaturated ring containing two heteroatoms. In another sub-embodiment A is a 5-membered monocyclic saturated or partially unsaturated ring containing three heteroatoms. In a still further sub-embodiment A is a 5-membered monocyclic saturated or partially unsaturated ring containing four heteroatoms. In another sub-embodiment, A is a 6-membered monocyclic saturated or partially unsaturated ring containing one heteroatom. In a further sub-embodiment, A is a 6-membered monocyclic saturated or partially unsaturated ring containing two heteroatoms. In another sub-embodiment A is a 6-membered monocyclic saturated or partially unsaturated ring containing three heteroatoms. In a still further sub-embodiment A is a 6-membered monocyclic saturated or partially unsaturated ring containing four heteroatoms.

A fourth embodiment (Embodiment E4) is a compound of Formula I, or a pharmaceutically acceptable salt thereof, wherein, A is a bicyclic saturated or partially unsaturated ring system, optionally substituted with up to four $R^8$, wherein from 1 to 4 of the ring atoms is independently O, N, or S and the remaining ring atoms are carbon atoms, and all other variables are as defined in the Summary of the Invention.

In a sub-embodiment of Embodiment E4, A is a bicyclic saturated or partially unsaturated ring system containing one heteroatom. In a further sub-embodiment, A is a bicyclic saturated or partially unsaturated ring system containing two heteroatoms. In another sub-embodiment A is a bicyclic saturated or partially unsaturated ring system containing three heteroatoms. In a still further sub-embodiment A is a bicyclic saturated or partially unsaturated ring system containing four heteroatoms.

In Embodiments E1-E4 and sub-embodiments of Embodiments E1-E4, A is optionally substituted with up to four occurrences of $R^8$. In sub-embodiments of Embodiments E1-E4 and preceding sub embodiments thereof, A is substituted with four occurrences of $R^8$, which are as originally defined. In another sub-embodiment, A is substituted with three occurrences of $R^8$. In a further sub-embodiment, A is substituted with two occurrences of $R^8$. In yet a further sub-embodiment, A is substituted with a single occurrence of $R^8$. In alternative embodiments of Embodiments E1-E4, A is unsubstituted.

A fifth embodiment (Embodiment E5) is a compound of Formula I, or a pharmaceutically acceptable salt thereof, wherein, A is selected from the group consisting of:

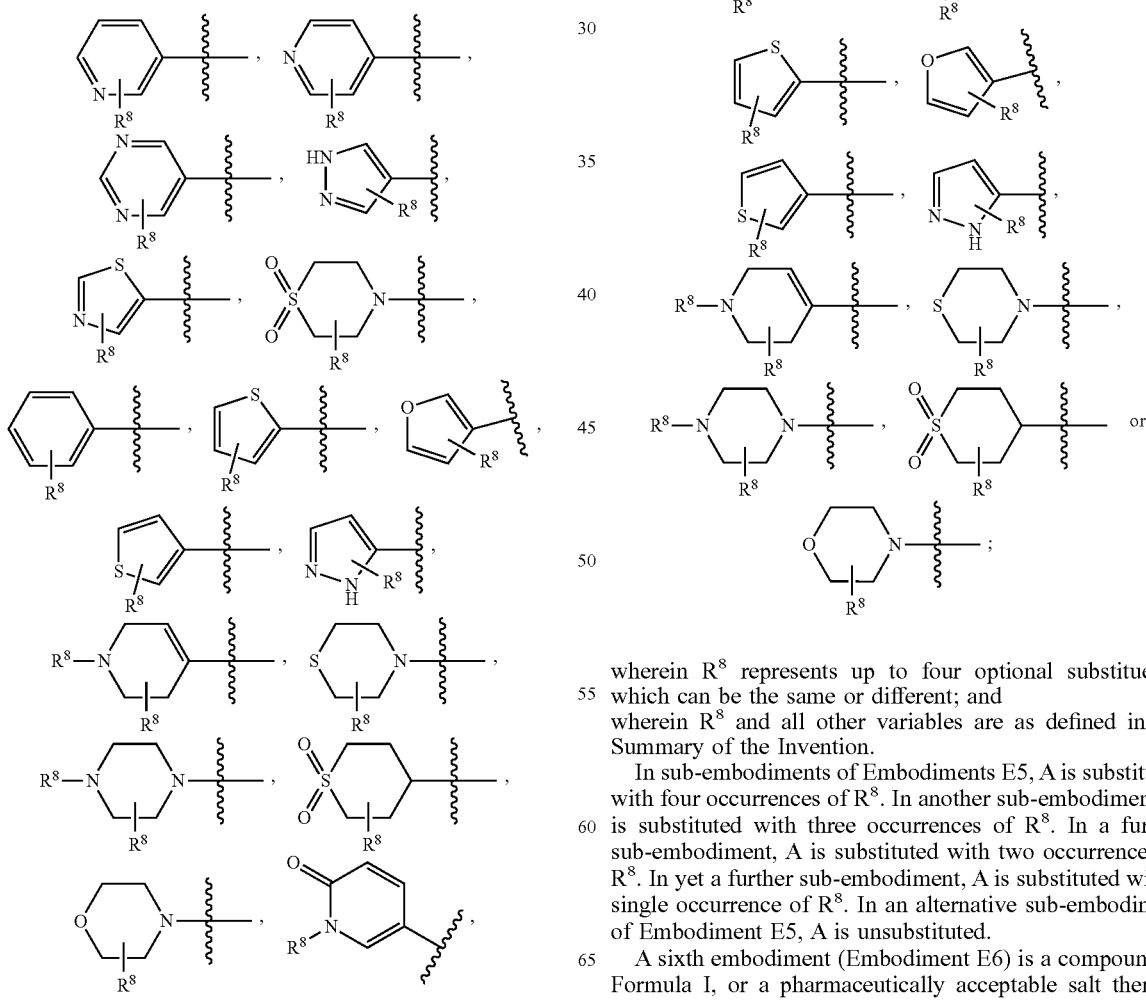

wherein $R^8$ represents up to four optional substituents, which can be the same or different; and
wherein $R^8$ and all other variables are as defined in the Summary of the Invention.

In sub-embodiments of Embodiments E5, A is substituted with four occurrences of $R^8$. In another sub-embodiment, A is substituted with three occurrences of $R^8$. In a further sub-embodiment, A is substituted with two occurrences of $R^8$. In yet a further sub-embodiment, A is substituted with a single occurrence of $R^8$. In an alternative sub-embodiment of Embodiment E5, A is unsubstituted.

A sixth embodiment (Embodiment E6) is a compound of Formula I, or a pharmaceutically acceptable salt thereof, wherein, A is selected from the group consisting of:

or wherein, A is selected from the group consisting of:

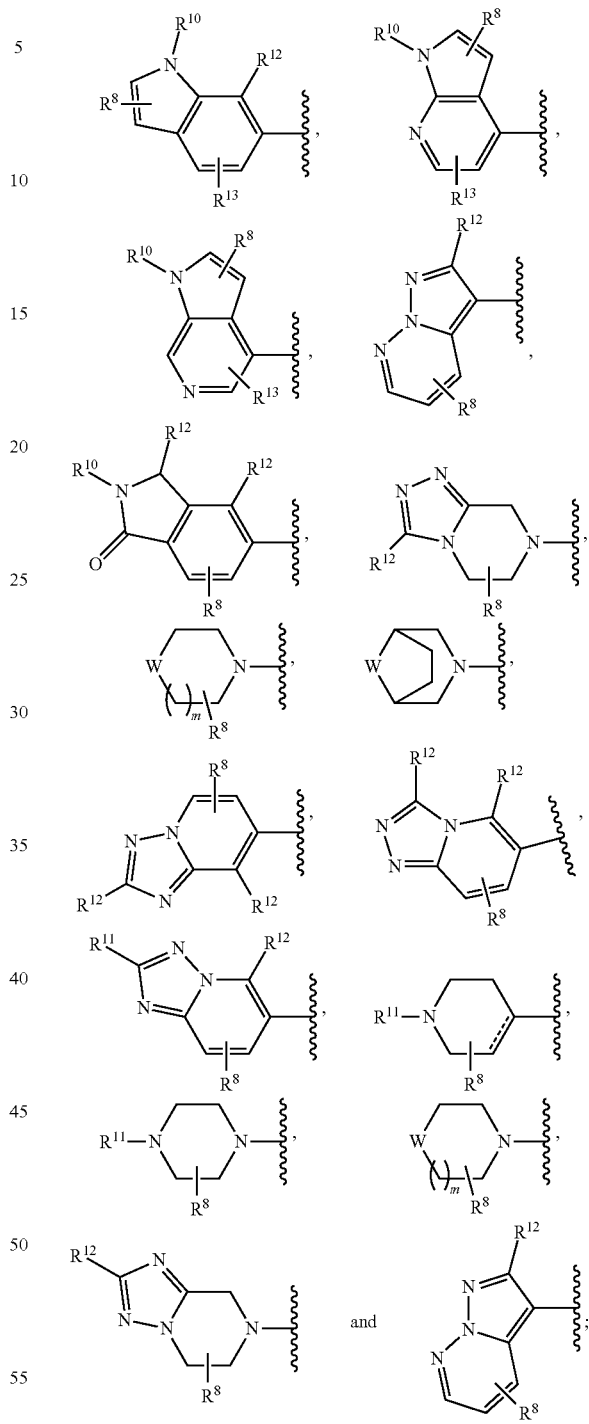

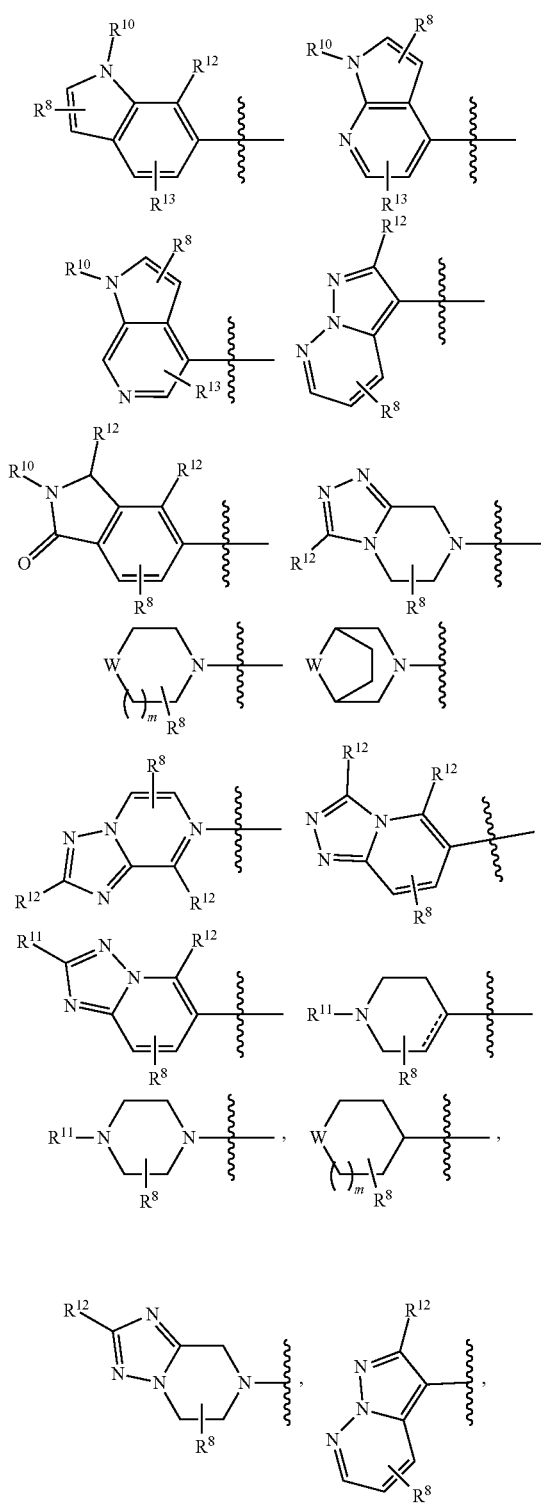

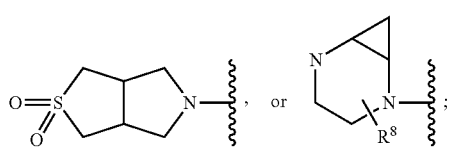

wherein:
m= is 0, 1, 2, or 3;
each occurrence of $R^8$ is independently selected from H, halogen, $C_1$-$C_6$ alkyl, $C_3$-$C_6$ cycloalkyl, $C_3$-$C_6$ heterocycloalkyl, —O$C_1$-$C_6$ alkyl, benzyl, —OCF$_3$, —OCHF$_2$, —OR$^3$, =O, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, —CO ($R^2$)$_2$ and —C($R^9$)$_2$N($R^2$)$_2$, wherein said $C_1$-$C_6$ alkyl, $C_3$-$C_6$ cycloalkyl, $C_3$-$C_6$ heterocycloalkyl, —O$C_1$-$C_6$ alkyl, and benzyl are optionally substituted with up to four F, —OCH$_3$, —OH, =O, NH$_2$, NHCH$_3$, SO$_2$R$^3$, and N(CH$_3$)$_2$;

$R^{10}$ is selected from H, $C_1$-$C_6$ alkyl and $C_3$-$C_6$ cycloalkyl, wherein said $C_1$-$C_6$ alkyl and said $C_3$-$C_6$ cycloalkyl are optionally substituted with from one to four substituents, which are independently selected from F, —OCH$_3$, —OH, NH$_2$, NHCH$_3$, and N(CH$_3$)$_2$;

$R^{11}$ is selected from H, $C_1$-$C_6$ alkyl and $C_3$-$C_6$ cycloalkyl, —COR$^9$, —COOR$^3$, —CON(R$^9$)$_2$, and —SO$_2$R$^9$;

each occurrence of $R^{12}$ is independently selected from H, halogen, $C_1$-$C_6$ alkyl, $C_3$-$C_6$ cycloalkyl, benzyl, —OCF$_3$, —OCHF$_2$, —OR$^3$, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, and —C(R$^9$)$_2$N(R$^2$)$_2$, wherein said $C_1$-$C_6$ alkyl, $C_3$-$C_6$ cycloalkyl, and benzyl are optionally substituted with up to four F, —OCH$_3$, —OH, NH$_2$, NHCH$_3$, and N(CH$_3$)$_2$;

$R^{13}$ is selected from H, halogen, $C_1$-$C_6$ alkyl, $C_3$-$C_6$ cycloalkyl, benzyl, —OCF$_3$, —OCHF$_2$, —OR$^3$, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, and —C(R$^9$)$_2$N(R$^2$)$_2$, wherein said $C_1$-$C_6$ alkyl, $C_3$-$C_6$ cycloalkyl, and benzyl are optionally substituted with up to four F, —OCH$_3$, —OH, NH$_2$, NHCH$_3$, and N(CH$_3$)$_2$; and W is selected from O, S, SO, SO$_2$, and S(=O)(=NH); and wherein = represents a double or a single bond, wherein all other variable are as defined in the Summary of the Invention.

In Embodiments E1-E6 and sub-embodiments of Embodiments E1-E6, each occurrence of $R^8$ is independently selected from H, halogen, $C_1$-$C_6$ alkyl, $C_3$-$C_6$ cycloalkyl, $C_3$-$C_6$ heterocycloalkyl, —O$C_1$-$C_6$ alkyl, benzyl, —OCF$_3$, —OCHF$_2$, —OR$^3$, =O, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, —CO(R$^2$)$_2$ and —C(R$^9$)$_2$N(R$^2$)$_2$, wherein said $C_1$-$C_6$ alkyl, $C_3$-$C_6$ cycloalkyl, $C_3$-$C_6$ heterocycloalkyl, —O$C_1$-$C_6$ alkyl, and benzyl are optionally substituted with up to four F, —OCH$_3$, —OH, =O, NH$_2$, NHCH$_3$, SO$_2$R$^3$, and N(CH$_3$)$_2$.

In a specific sub-embodiment of Embodiments E1-E6, one or more occurrences of $R^8$ is selected from: —H, —OH, —CN, —CH$_3$, —CH$_2$NH$_2$, —CONH$_2$, C(CH$_3$)$_2$OH, —COOC(CH$_3$)$_2$CH$_3$, —SCH$_3$, —OCH$_3$, —C$_1$, —F, —CHF$_2$, =O, -cyclopropyl, NO$_2$, —NHSO$_2$CH$_3$, —SO$_2$N(CH$_3$)$_2$, —S(=O)(=NH)CH$_3$, —SO$_2$CH$_3$, —SOCH$_3$, —SO$_2$NH$_2$, —OCH$_2$CH$_2$OH, COCH$_3$, COcyclopropyl and

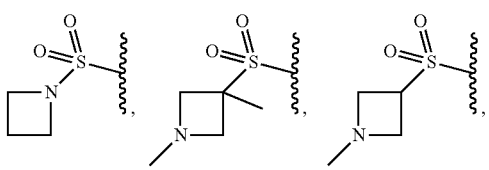

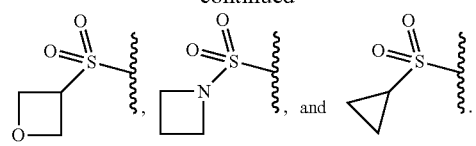

In another specific sub-embodiment of Embodiments E1-E6, one or more occurrences of $R^8$ is selected from:

—SOCH$_3$, —SO$_2$CH$_3$, oxo, —H, —SCH$_3$, —OH, —SO$_2$N(CH$_3$)$_2$, —SO$_2$NH$_2$, —CONH$_2$, —O(CH$_2$)$_2$OH, and —F.

A seventh embodiment (Embodiment E7) is a compound of Formula I, or a pharmaceutically acceptable salt thereof, wherein, A is as defined in the Summary of the Invention or in any of Embodiments E1-E6, E is a 6-membered aryl, wherein said aryl is optionally substituted with up to four substituents, which are independently selected from halogen, —CH$_3$, —SOCH$_3$, —SO$_2$CH$_3$, —H, —SCH$_3$, —OH, —SO$_2$N(CH$_3$)$_2$, —SO$_2$NH$_2$, —CONH$_2$ and —O(CH$_2$)$_2$OH, and all other variables are as defined in the Summary of the Invention.

An eighth embodiment (Embodiment E8) is a compound of Formula I, or a pharmaceutically acceptable salt thereof, wherein, A is as defined in the Summary of the Invention or in any of Embodiments E1-E6, E is a 6-membered or 9-membered heterocycle containing from one to three heteroatoms independently selected from S, O, and N, wherein said heterocycle is unsubstituted or substituted with up to four substituents, which are independently selected from halogen, and =O, and all other variables are as defined in the Summary of the Invention.

A ninth embodiment (Embodiment E9) is a compound of Formula I, or a pharmaceutically acceptable salt thereof, wherein, A is as defined in the Summary of the Invention or in any of Embodiments E1-E6, E is a 6-membered heteroaryl containing from one to three heteroatoms independently selected from S, O, and N, wherein said heteroaryl is optionally substituted with up to four substituents, which are independently selected from halogen, —CN, —CF$_3$, —CHF$_2$, —CH$_2$NH$_2$, —CH$_2$NHCOCH$_3$, —OCF$_3$, —OCHF$_2$, —OH, —O—(C$_1$-C$_6$)alkyl, $C_1$-$C_6$ alkyl, and $C_3$-$C_6$ cycloalkyl, and all other variables are as defined in the Summary of the Invention.

A tenth embodiment (Embodiment E10) is a compound of Formula I, or a pharmaceutically acceptable salt thereof, wherein, A is as defined in the Summary of the Invention or in any of Embodiments E1-E6, E is:

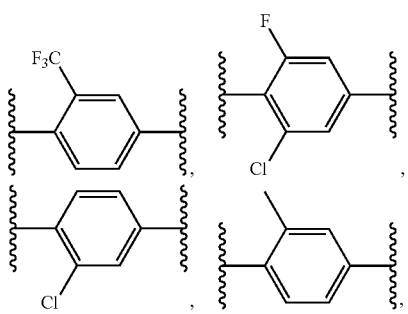

-continued

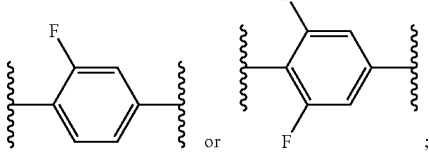

and all other variables are as defined in the Summary of the Invention, or

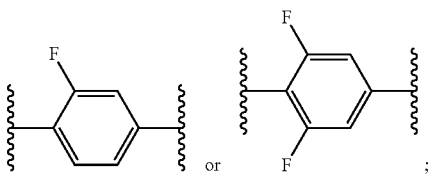 [SMILES: *c1ccc(*)c(F)c1 ; *c1cc(F)c(*)c(F)c1]

and all other variables are as defined in the Summary of the Invention.

An eleventh embodiment (Embodiment E11) is a compound of Formula I, or a pharmaceutically acceptable salt thereof, wherein, A is as defined in the Summary of the Invention or in any of Embodiments E1-E6, E is:

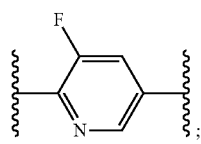

and all other variables are as defined in the Summary of the Invention.

A twelfth embodiment (Embodiment E12) is a compound of Formula I, or a pharmaceutically acceptable salt thereof, wherein, A is as defined in the summary of the invention or in any of Embodiments E1-E6, E is:

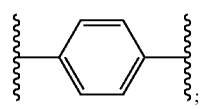 [SMILES: *c1ccc(*)cc1]

and all other variables are as originally defined.

A thirteenth embodiment (Embodiment E13) is a compound of Formula IA, or a pharmaceutically acceptable salt thereof, having the formula:

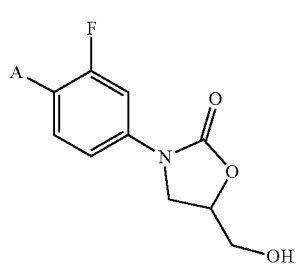

(IA)

wherein:
A is as defined in any of Embodiments E1-E6.

A fourteenth embodiment (Embodiment E14) is a compound of Formula IB, or a pharmaceutically acceptable salt thereof, having the formula:

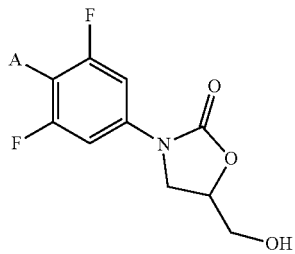

(IB)

wherein:
A is as defined in any of Embodiments E1-E6.
In sub-embodiments of Embodiments, A is:

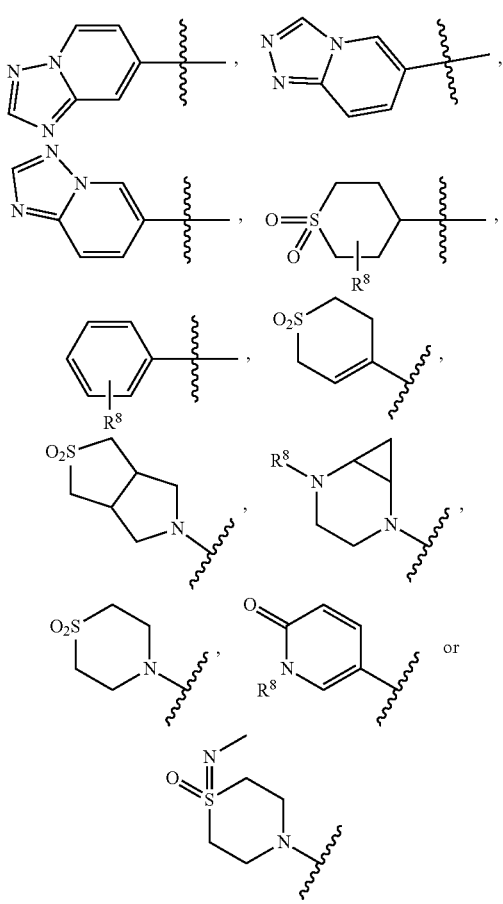

wherein $R^8$ represents one, two, three or four optional ring carbon substituents, which can be the same or different.

In sub-embodiments of Embodiments, $R^8$ is —OH, —CN, —CH$_3$, —CH$_2$NH$_2$, —CONH$_2$, C(CH$_3$)$_2$OH, —COOC(CH$_3$)$_2$CH$_3$, —SCH$_3$, —OCH$_3$, —C$_1$, —F, —CHF$_2$, =O, -cyclopropyl, NO$_2$, —NHSO$_2$CH$_3$, —SO$_2$N(CH$_3$)$_2$, —S(=O)(=NH)CH$_3$, —SO$_2$CH$_3$, —SOCH$_3$, —SO$_2$NH$_2$, —OCH$_2$CH$_2$OH, COCH$_3$, COcyclopropyl and

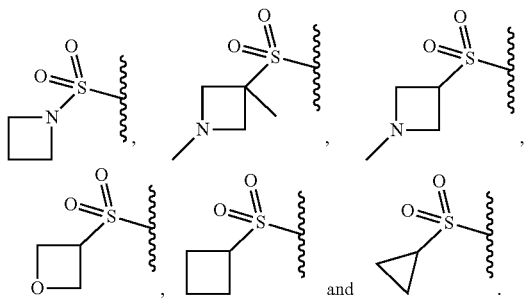

In sub-embodiments of Embodiments, A is:

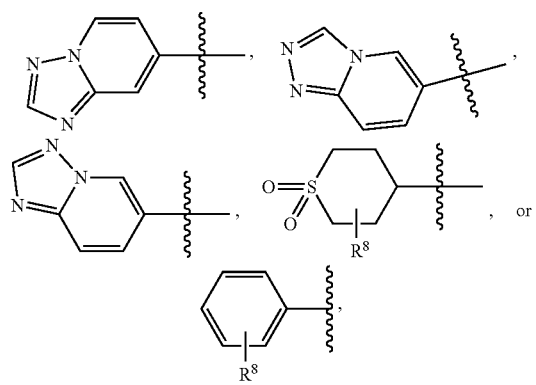

wherein $R^8$ represents one, two, three or four optional ring carbon substituents, which can be the same or different.

In sub-embodiments of Embodiments, $R^8$ is halogen, —SOCH$_3$, —SO$_2$CH$_3$, —SONH$_2$, —H, —SCH$_3$, —OH, —SO$_2$N(CH$_3$)$_2$, —CONH$_2$ or —O(CH$_2$)$_2$OH.

In sub-embodiments of Embodiments, A is:

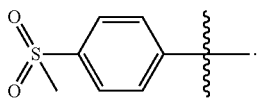

In sub-embodiments of Embodiments, A is:

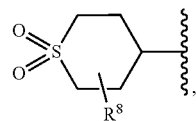

wherein $R^8$ represents one, two, three or four optional ring carbon substituents, which can be the same or different.

In sub-embodiments of Embodiments, $R^8$ is halogen or —SO$_2$CH$_3$.

In sub-embodiments of Embodiments, A is:

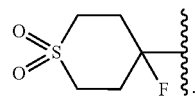

In another aspect the present invention includes compounds, or pharmaceutically acceptable salts thereof, having the structure:

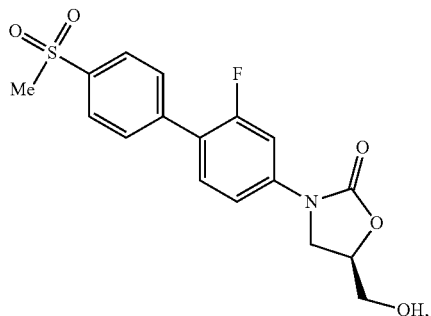

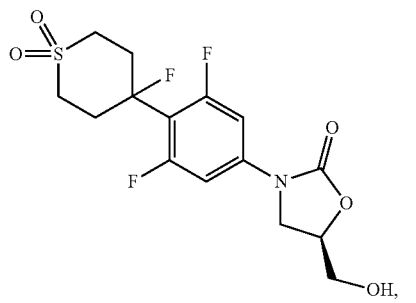

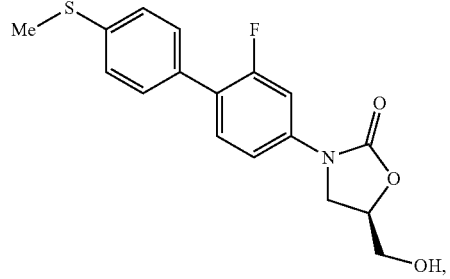

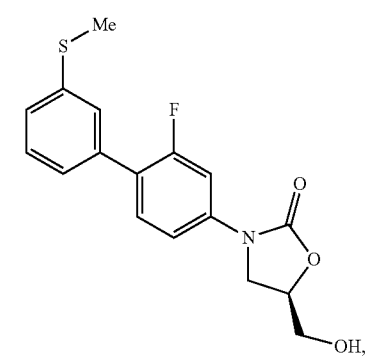

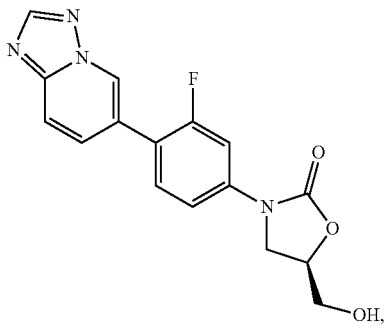

17
-continued
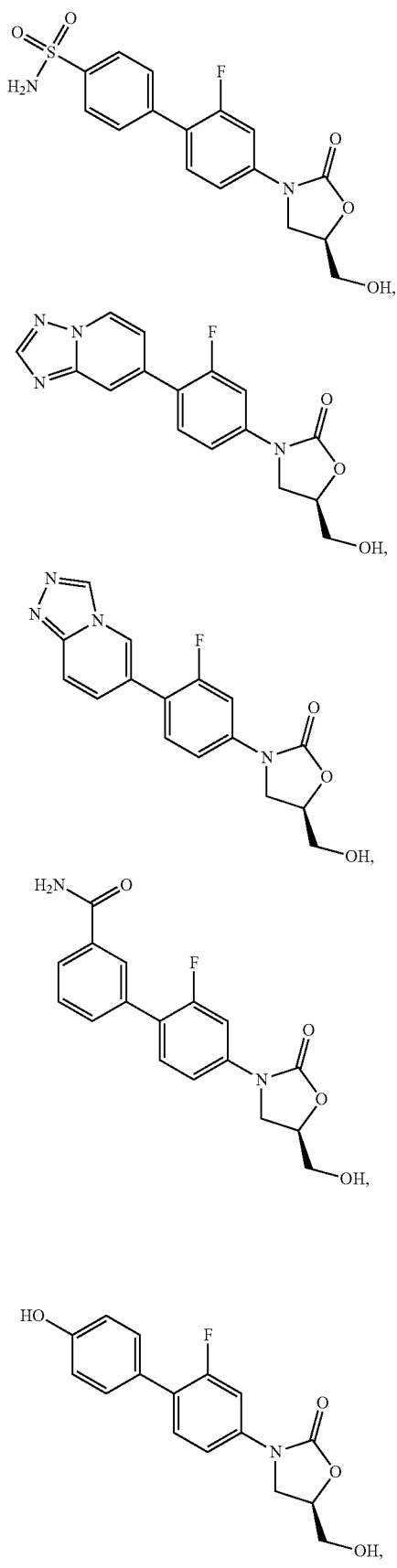
18
-continued
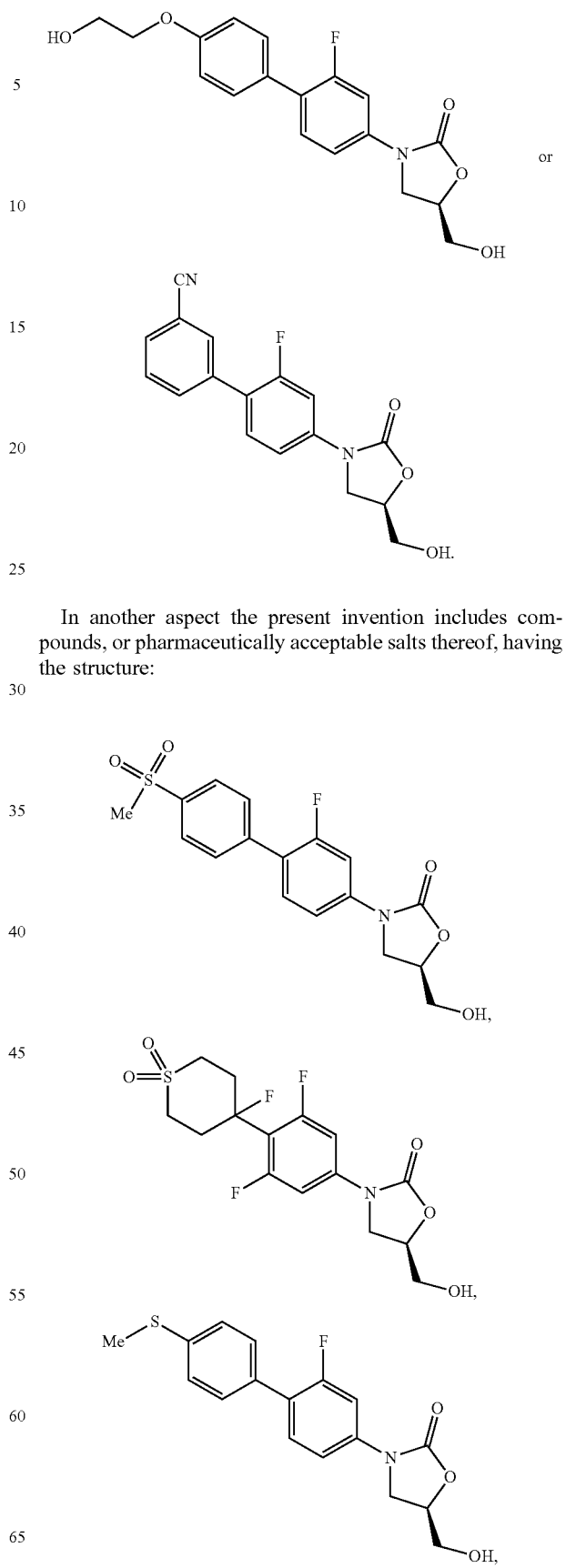
In another aspect the present invention includes compounds, or pharmaceutically acceptable salts thereof, having the structure:

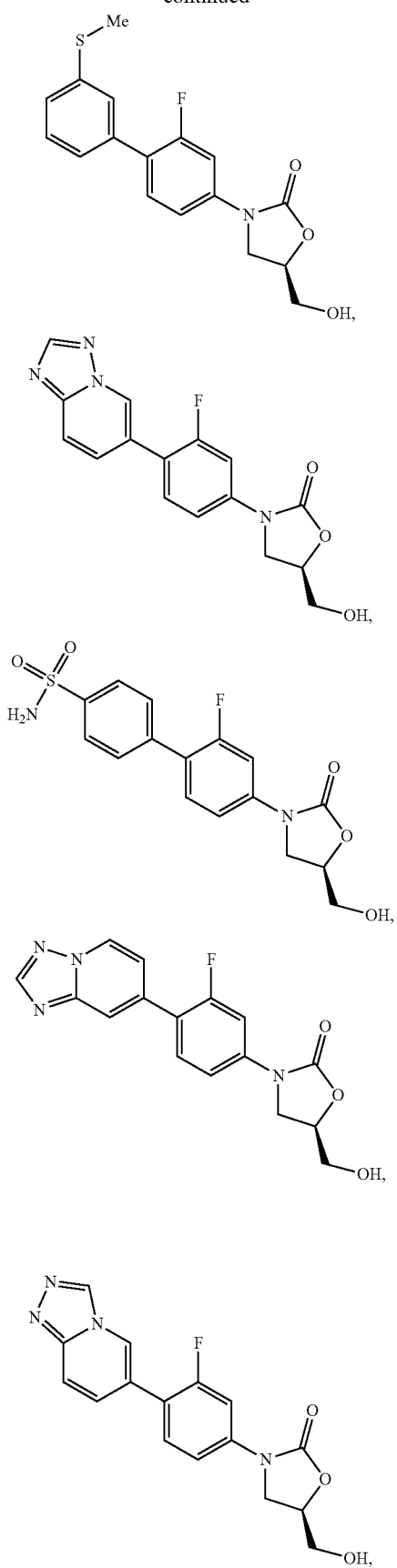
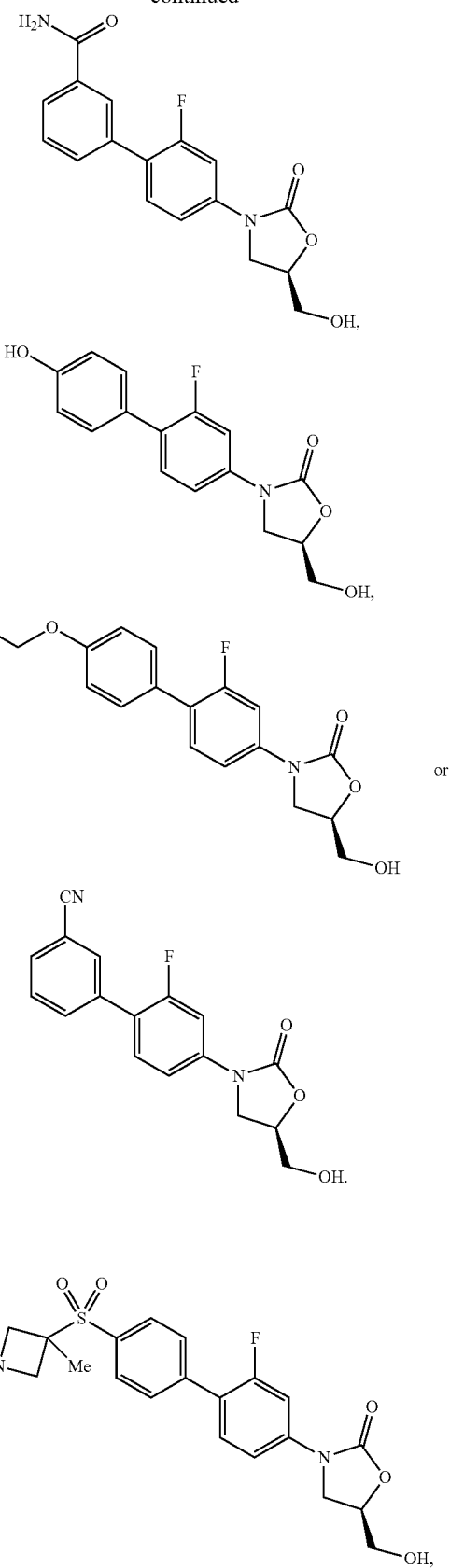

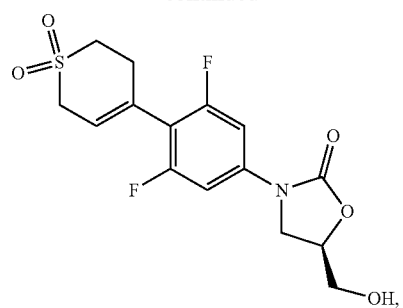
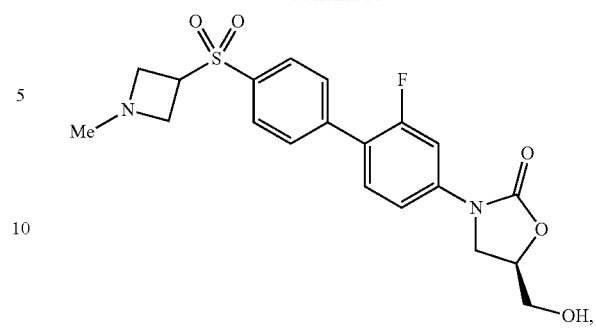
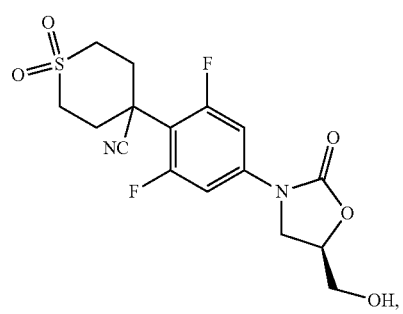
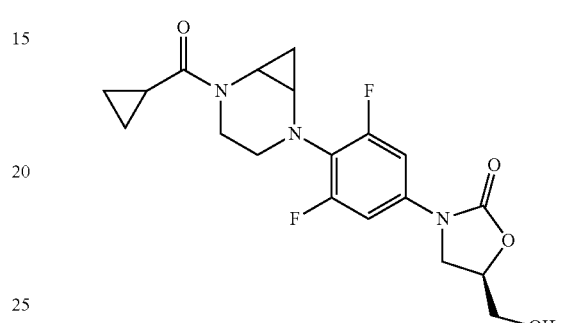
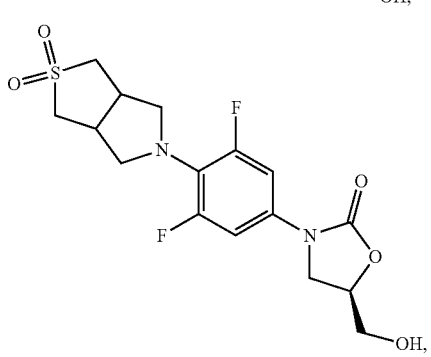
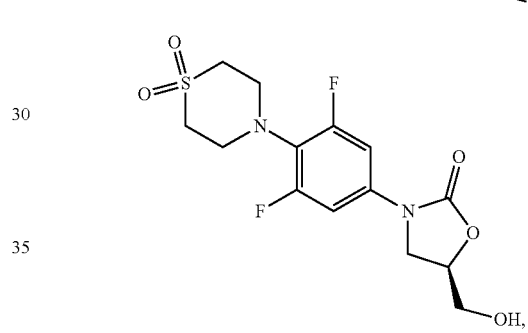
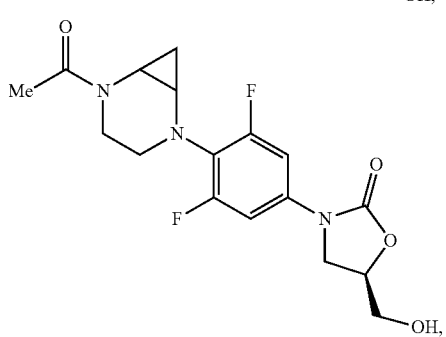
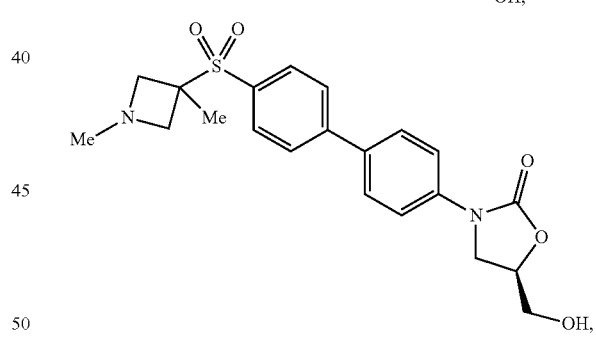
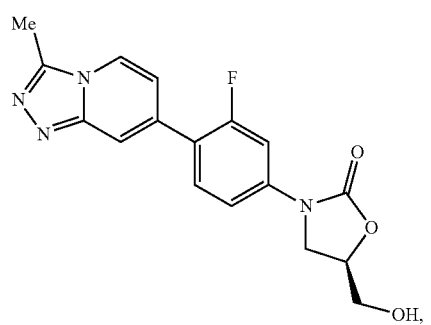
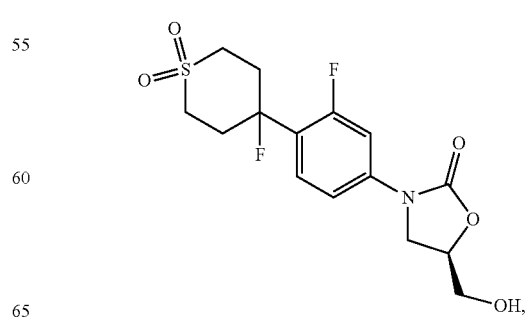

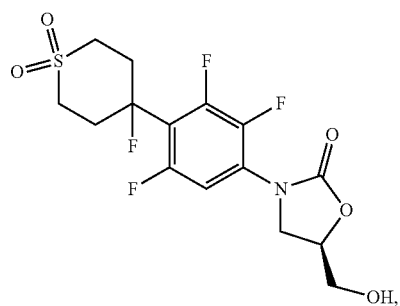
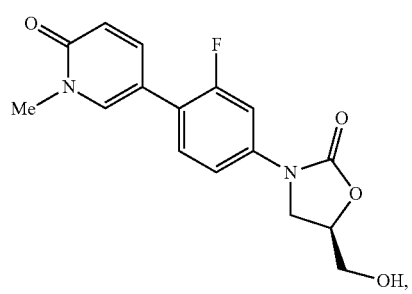
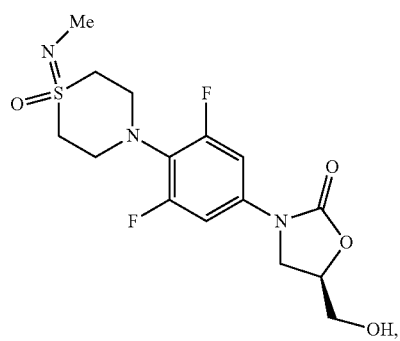
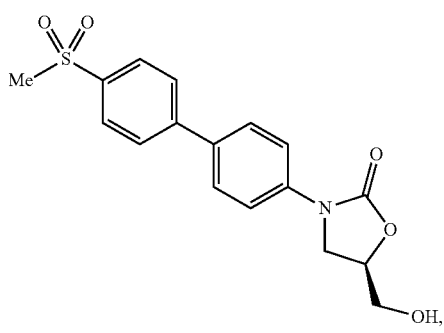
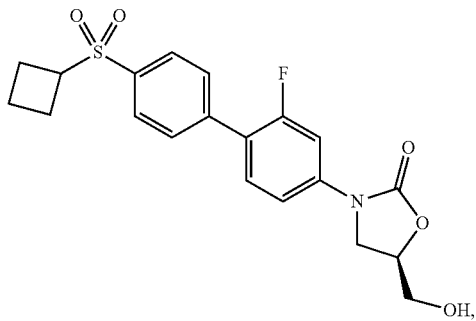
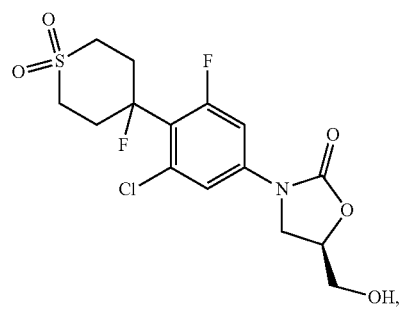
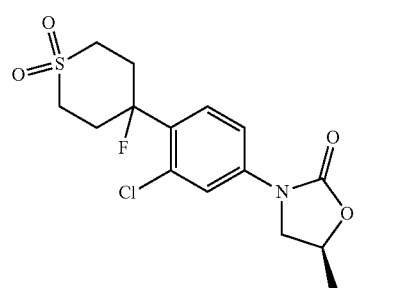
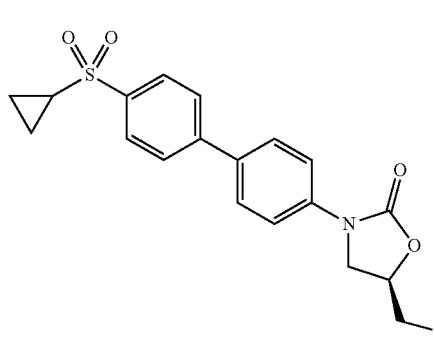
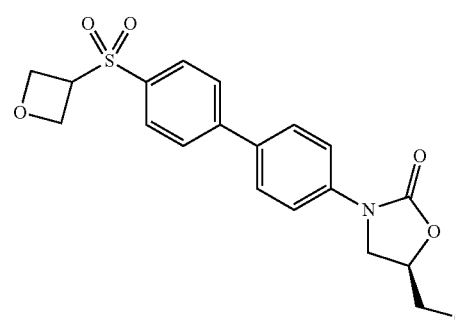
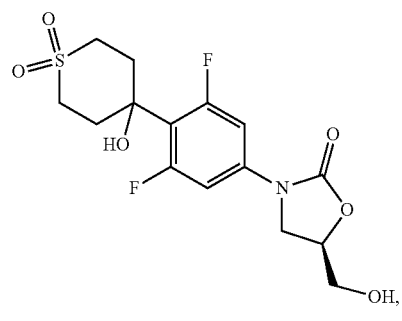

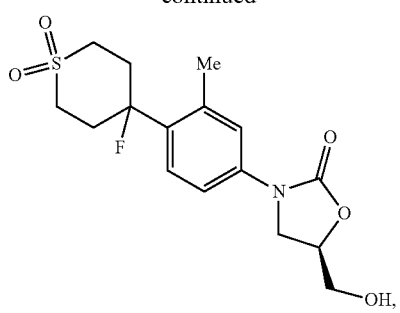
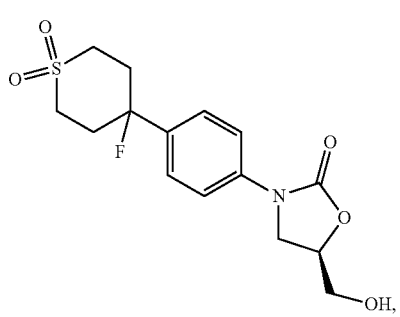
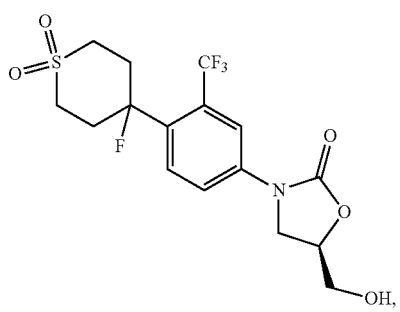
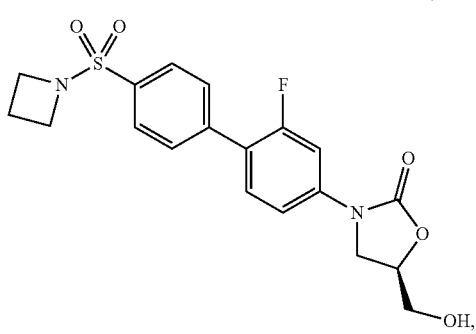
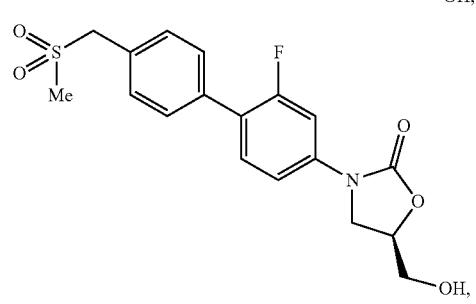
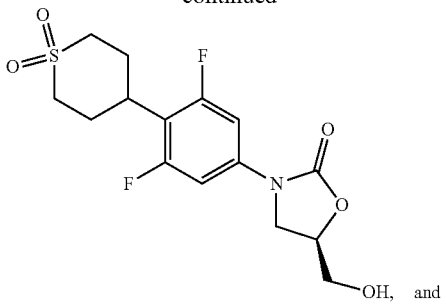
In certain embodiments, the present invention includes compounds, or pharmaceutically acceptable salts thereof, having the structure:
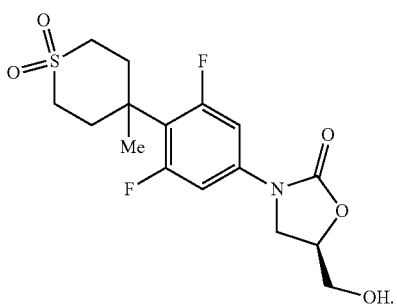
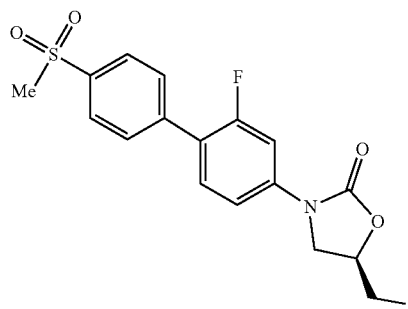
or
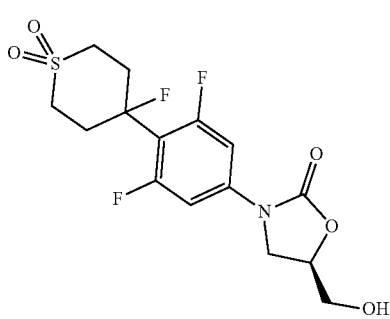
Also described herein are prodrugs of the compounds of Formula I, represented by Formula II:

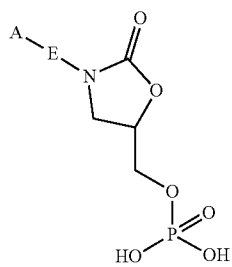

wherein embodiments of A and E are described above.

Also described herein are prodrugs of the compounds of Formula I, represented by Formula III:

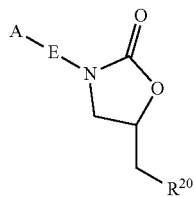

wherein R20 is OH or —OP=O(OH)$_2$ and embodiments of A and E are described above.

Also described herein are the following of Formula IIA and IIB:

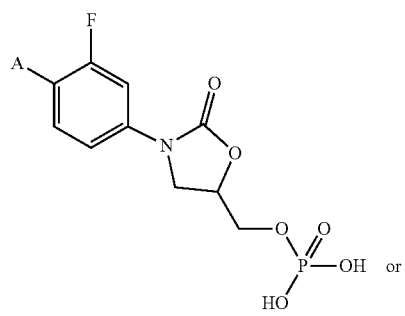

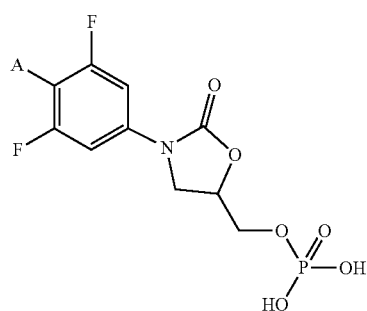

wherein the embodiments of A are described above.

Also described herein is the following compound:

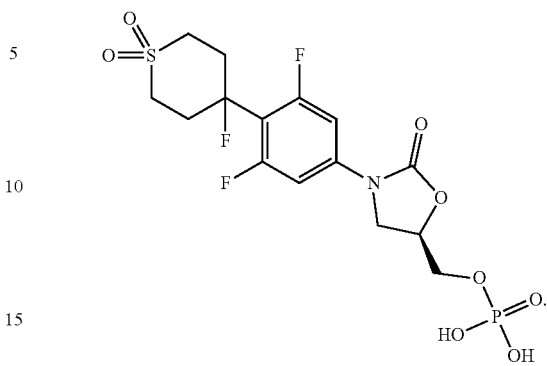

Reference to different embodiments with respect to Formula I compounds, specifically includes different embodiments of Formula I such as Formula IA and Formula IB, sub-embodiments of Formula IA and Formula IB, other embodiments provided herein, and individual compounds described herein.

Other embodiments of the present invention include the following:
(a) A pharmaceutical composition comprising an effective amount of a compound of Formula I, IA, IB or Formula II, IIA, IIB as defined herein, or a pharmaceutically acceptable salt thereof, and a pharmaceutically acceptable carrier.
(b) The pharmaceutical composition of (a), further comprising a second compound, wherein the second compound is an antibiotic.
(c) The pharmaceutical composition of (b), wherein the second compound is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terididone, para-aminosalicylic acid, clofazimine, clarithromycin, amoxicillin-clavulanate, thiacetazone, meropenem-clavulanate, GSK 3036656, M72/AS01E vaccine and thioridazine.
(d) A pharmaceutical composition comprising (i) a compound of Formula I, IA, IB or Formula II, IIA, IIB or a pharmaceutically acceptable salt thereof, and (ii) a second compound, wherein the second compound is an antibiotic, wherein the compound of Formula I, IA, IB or Formula II, IIA, IIB and the second compound are each employed in an amount that renders the combination effective for treating or preventing bacterial infection.
(e) The combination of (d), wherein the second compound is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terididone, para-aminosalicylic acid, clofazimine, clarithromycin, amoxicillin-clavulanate, thiacetazone, meropenem-clavulanate, and thioridazine.
(f) A method for treating a bacterial infection in a subject which comprises administering to a subject in need of such treatment an effective amount of a compound of Formula I, IA, IB or Formula II, IIA, IIB or a pharmaceutically acceptable salt thereof.
(g) A method for preventing and/or treating a bacterial infection which comprises administering to a subject in need of such treatment an effective amount of a compound of Formula I, IA, IB or Formula II, IIA, IIB or a pharmaceutically acceptable salt thereof.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to *Mycobacterium tuberculosis*.

(j) A method for preventing and/or treating a mycobacterial infection which comprises administering to a subject in need of such treatment an effective amount of a composition comprising an Oxazolidinone Compound, or a pharmaceutically acceptable salt thereof.

(k) The method of treating a mycobacterial infection as set forth in (j), wherein the mycobacterial infection is due to *M. tuberculosis*.

(l) The method of treating a mycobacterial infection as set forth in (j), wherein the composition is a composition of (a), (b), (c), (d), or (e).

(m) The method of treating a bacterial infection as set forth in (f), (g), or (h), wherein the bacterial infection is due to *Mycobacterium abscessus, Mycobacterium chelonae, Mycobacterium fortuitum, Mycobacterium intracellulare, Mycobacterium kansasii, Mycobacterium marinum* and/or *Mycobacterium avium*.

The present invention also includes a compound of Formula I, IA, IB or Formula II, IIA, IIB or a pharmaceutically acceptable salt thereof, (i) for use in, (ii) for use as a medicament for, or (iii) for use in the preparation (or manufacture) of a medicament for, medicine or treating bacterial infection, particularly a mycobacterial infection. In these uses, the compounds of the present invention can optionally be employed in combination with one or more second therapeutic agents including ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, teridithone, para-aminosalicylic acid, clofazimine, clarithromycin, amoxicillin-clavulanate, thiacetazone, meropenem-clavulanate, GSK 3036656, M72/AS01E vaccine and thioridazine.

Additional embodiments of the invention include the pharmaceutical compositions, combinations and methods set forth in (a)-(l) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, IA, or IB or its salt and a pharmaceutically acceptable carrier and optionally one or more excipients, it is understood that the term "substantially pure" is in reference to a compound of Formula I, IA, or IB or its salt per se; i.e., the purity of the active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

"About", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

"Aromatic ring system" means monocyclic, bicyclic or tricyclic aromatic ring or ring system containing 5-14 ring atoms, wherein at least one of the rings is aromatic. Aromatic ring systems, as used herein, encompass aryls and heteroaryls. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In another example, a heteromonocyclic ring is fused through two ring atoms to a phenyl or 5-6-membered heteroaryl containing 1, 2, or 3 heteroatoms selected from N, O, and S.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, and the like.

The term "heterocycloalkyl," as used herein, refers to a non-aromatic saturated monocyclic or multicyclic ring system comprising 3 to 11 ring atoms, wherein from 1 to 4 of the ring atoms are independently O, S, or N, and the remainder of the ring atoms are carbon atoms. A heterocycloalkyl group can be joined via a ring carbon or ring nitrogen atom (if present). In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl (if present) can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, tetrahydro-2H-thiopyran 1,1-dioxide, silapyrrolidine and the like, and all isomers thereof.

As used herein, e.g. in the definition of $R^8$, "—$CONH_2$" means "—C=$ONH_2$".

"Drug resistant" means, in connection with a *Mycobacterium*, a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

"Halogen" includes fluorine, chlorine, bromine and iodine.

"Heteroaryl", as used herein, refers to an monocyclic or multicyclic ring system comprising about 5 to about 14 ring atoms, wherein from 1 to 4 of the ring atoms is independently O, N, or S and the remaining ring atoms are carbon atoms, wherein at least one of the heteroatom containing rings is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. In another embodiment of the present invention, heteroaryl is pyridine. Examples of bicyclic rings include:

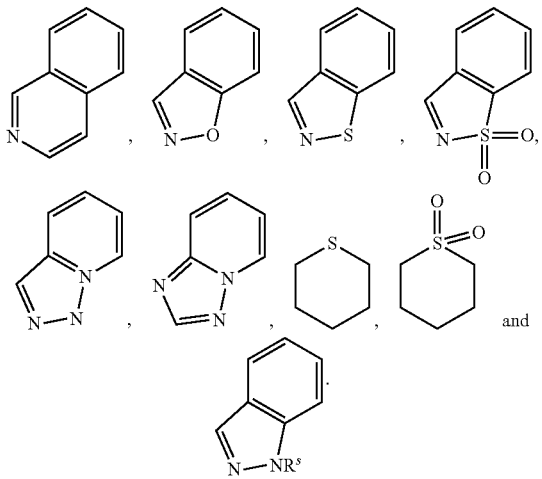

"Heterocycle" means a monocyclic or bicyclic saturated, partially unsaturated, or unsaturated ring system containing 5-10 atoms and containing at least one ring heteroatom selected from N, S and O. In select embodiments, the ring system contains 1-4 heteroatoms selected from N, S and O. When a heterocycle contains two rings, the rings may be fused, bridged or spirocyclic. Examples of monocyclic heterocycle rings include piperazine, piperidine, and morpholine. Examples of bicyclic heterocycle rings include 1,4-diazabicyclo[2,2,2]octane and 2,6-diazaspiroheptane. Heterocycles include heteroaryls and heterocycloalkyls.

"Oxo" means an oxygen atom connected to another atom by a double bond and is can be represented "=O".

"Tuberculosis" comprises disease states usually associated with infections caused by mycobacteria species comprising *M. tuberculosis* complex. The term "tuberculosis" is also associated with mycobacterial infections caused by mycobacteria other than *M. tuberculosis* (MOTT). Other mycobacterial species include *M. avium-intracellulare, M. kansarii, M. fortuitum, M. chelonae, M. leprae, M. africanum*, and *M. microti, M. avium* paratuberculosis, *M. intracellulare, M. scrofulaceum, M. abscessus, M. avium, M. xenopi, M. marinum*, and *M. ulcerans*.

Another embodiment of the present invention is a compound of Formula I, IA, IB or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, IA, or IB or a salt of Formula I, IA, or IB (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention encompasses all stereoisomeric forms of the compounds of Formula I, Formula IA and Formula IB. Unless a specific stereochemistry is indicated, the present invention is meant to comprehend all such isomeric forms of these compounds. Centers of asymmetry that are present in the compounds of Formula I, Formula IA, and Formula IB can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula IA, or Formula IB or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^2$, $R^3$, etc., are to be chosen in conformity with well-known principles of chemical structure connectivity and stability.

The term "substituted" means that one or more hydrogens on the designated atom is replaced with a selection from the indicated group, provided that the designated atom's normal valency under the existing circumstances is not exceeded, and that the substitution results in a stable compound. The term substituted shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

By "stable compound" or "stable structure" is meant a compound that is sufficiently robust to survive isolation to a useful degree of purity from a reaction mixture, and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I, IA and IB.

When a group, e.g., $C_1$-$C_8$ alkyl, is indicated as being substituted, such substitutions can also occur where such group is part of a larger substituent, e.g., —$C_1$-$C_6$alkyl-$C_3$-$C_7$cycloalkyl and —$C_1$-$C_8$alkyl-aryl.

In the compounds of Formula I, IA, and IB, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, IA, and IB. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, IA, and IB can be prepared without undue experimentation by conventional techniques well known to those skilled in the art or by processes analogous to those described in the EXAMPLES herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_{1-6}$ when used with a chain, for example an alkyl chain, means that the chain can contain 1, 2, 3, 4, 5 or 6 carbon atoms. It also includes all ranges contained therein including $C_{1-5}$, $C_{1-4}$, $C_{1-3}$, $C_{1-2}$, $C_{2-6}$, $C_{3-6}$, $C_{4-6}$, $C_{5-6}$, and all other possible combinations.

It should also be noted that any carbon as well as heteroatom with unsatisfied valences in the text, schemes, examples and tables herein is assumed to have the sufficient number of hydrogen atom(s) to satisfy the valences.

When any substituent or variable (e.g., alkyl, $R^8$, $R^{11}$, etc.) occurs more than one time in any constituent or in Formula (I), its definition on each occurrence is independent of its definition at every other occurrence, unless otherwise indicated. Also, combinations of substituents and/or variables are permissible only if such combinations result in stable compounds. A squiggly line across a bond in a substituent variable represents the point of attachment.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The compounds of the invention can also be employed in the form of a prodrug. For example, the hydrogen in —COOH be replaced with any the following groups: $C_{1-6}$ alkyl, $C_{3-6}$ cycloalkyl, $-C_{1-6}$alkyl-$C_{3-6}$cycloalkyl, $C_{3-7}$ cycloheteroalkyl, $-C_{1-6}$alkyl-$C_{3-7}$cycloheteroalkyl, aryl, $-C_{1-10}$alkyl-aryl, heteroaryl, and $-C_{1-10}$ alkyl-heteroaryl. Any $C_{1-6}$ alkyl, $C_{3-6}$ cycloalkyl, or $C_{3-7}$ cycloheteroalkyl can also be substituted. Any aryl or heteroaryl can also be substituted as indicated.

As set forth above, the present invention includes pharmaceutical compositions comprising a compound of Formula I, IA, or IB of the present invention, optionally one or more other active components, and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, IA, or IB or a pharmaceutically acceptable salt thereof. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I, IA or IB mean providing the compound, or a pharmaceutically acceptable salt thereof, to the individual in need of treatment. When a compound or a salt thereof is provided in combination with one or more other active agents, "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein with respect to an oxazolidinone compound means the amount of active compound sufficient to cause a bacteriocidal or bacteriostatic effect. In one embodiment, the effective amount is a "therapeutically effective amount" meaning the amount of active compound that can overcome bacterial drug resistance and which is sufficient to inhibit bacterial replication and/or result in bacterial killing. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, $21^{st}$ edition, 2006. In one embodiment, compounds of the invention are administered intravenously in a hospital setting. In another embodiment, administration is oral in the form of a tablet or capsule or the like. The dosage of the compounds of the invention and of their pharmaceutically acceptable salts may vary within wide limits and should naturally be adjusted, in each particular case, to the individual conditions and to the pathogenic agent to be controlled. In general, for a use in the treatment of bacterial infections, the daily dose may be between 0.005 mg/kg to 100 mg/kg, 0.01 mg/kg to 10 mg/kg, 0.05 mg/kg to 5 mg/kg, 0.05 mg/kg to 1 mg/kg.

In some embodiments, the compound of the invention is provided in a pharmaceutical formulation for oral, intravenous, intramuscular, nasal, or topical administration. Thus, in some embodiments, the formulation can be prepared in a dosage form, such as but not limited to, a tablet, capsule, liquid (solution or suspension), suppository, ointment, cream, or aerosol. In some embodiments, the presently disclosed subject matter provides such compounds and/or formulations that have been lyophilized and that can be reconstituted to form pharmaceutically acceptable formulations for administration, for example, as by intravenous or intramuscular injection.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Infections that may be treatable by the compounds of the invention can be caused by a variety of microbes, including fungi, algae, protozoa, bacteria, and viruses. In some embodiments, the infection is a bacterial infection. Exemplary microbial infections that may be treated by the methods of the invention include, but are not limited to, infections caused by one or more of *Staphylococcus aureaus, Entero-*

*coccus faecalis, Bacillus anthracis,* a *Streptococcus* species (e.g., *Streptococcus pyogenes* and *Streptococcus pneumoniae*), *Escherichia coli, Pseudomonas aeruginosa, Burkholderia cepacia,* a *Proteus* species (e.g., *Proteus mirabilis* and *Proteus vulgaris), Klebsiella pneumoniae, Acinetobacter baumannii, Strenotrophomonas maltophillia, Mycobacterium tuberculosis, Mycobacterium bovis,* other mycobacteria of the tuberculosis complex, and non-tuberculous mycobacteria, including *Mycobacterium ulcerans, Mycobacterium abscessus,* and *Mycobacterium avium.*

In certain embodiments, the infection is an infection of a gram-positive bacterium. In some embodiments, the infection is selected from a mycobacterial infection, a *Bacillus anthracis* infection, an *Enterococcus faecalis* infection, and a *Streptococcus pneumoniae* infection.

In some embodiments, the compound of Formula I, IA, or IB is administered prophylactically to prevent or reduce the incidence of one of: (a) a *Mycobacterium tuberculosis* infection in a subject at risk of infection; (b) a recurrence of a *Mycobacterium tuberculosis* infection; and (c) combinations thereof. In some embodiments, the compound of Formula I, IA, or IB is administered to treat an existing *Mycobacterium tuberculosis* infection. In some embodiments, the compound of Formula I, IA, or IB is administered to treat an infection of a multi-drug resistant strain of *Mycobacterium tuberculosis* (i.e., a strain that is resistant to two or more previously known anti-tuberculosis drugs, such as isoniazid, ethambutol, rifampicin, kanamycin, capreomycin, linezolid, and streptomycin). In some embodiments, the compound of Formula (I) has a minimum inhibitory concentration (MIC) against *Mycobacterium tuberculosis* of 25 µg/mL or less. In some embodiments, the compound of Formula I, IA or IB is administered to treat an infection of a multi-drug resistant strain of *Mycobacterium tuberculosis.*

Thus, the methods of the presently disclosed subject matter can be useful for treating tuberculosis in that they inhibit the onset, growth, or spread of a TB infection, cause regression of the TB infection, cure the TB infection, or otherwise improve the general well-being of a subject afflicted with, or at risk of, contracting tuberculosis.

Subjects suffering from an *M. tuberculosis* or other tuberculosis-related infection can be determined via a number of techniques, e.g., sputum smear, chest X-ray, tuberculin skin test (i.e., Mantoux test or PPD test) and/or the presence of other clinical symptoms (e.g., chest pain, coughing blood, fever, night sweats, appetite loss, fatigue, etc.). If desired, bacterial RNA, DNA or proteins can be isolated from a subject believed to be suffering from TB and analyzed via methods known in the art and compared to known nucleic or amino acid sequences of bacterial RNA, DNA or protein.

In some embodiments, the compound of Formula I, IA, or IB has a minimum inhibitory concentration (MIC) against *Mycobacterium tuberculosis* of 25 µg/mL or less. MICS can be determined via methods known in the art, for example, as described in Hurdle et al., 2008, *J. Antimicrob. Chemother.* 62:1037-1045.

In some embodiments, the methods of the invention further comprise administering to the subject an additional therapeutic compound. In some embodiments, the compound of the invention is administered to the subject before, after, or at the same time as one or more additional therapeutic compounds. In some embodiments, the additional therapeutic compound is an antibiotic. In some embodiments, the additional therapeutic compound is an anti-tuberculosis therapeutic. In some embodiments, the additional therapeutic compound is selected from the group comprising isoniazid, ethambutol, rifampicin, kanamycin, capreomycin, linezolid, and streptomycin.

The invention thus provides in a further aspect, a combination comprising a compound of Formula I, IA, or IB or a pharmaceutically acceptable salt thereof, together with one or more additional therapeutic agents. Examples of such one or more additional therapeutic agents are anti-tuberculosis agents including, but not limited to, amikacin, aminosalicylic acid, capreomycin, cycloserine, ethambutol, ethionamide, isoniazid, kanamycin, pyrazinamide, rifamycins (such as rifampin, rifapentine and rifabutin), streptomycin, clarithromycin, azithromycin, oxazolidinones and fluoroquinolones (such as ofloxacin, ciprofloxacin, moxifloxacin and gatifloxacin). Such chemotherapy is determined by the judgment of the treating physician using preferred drug combinations. "First-line" chemotherapeutic agents used to treat a *Mycobacterium tuberculosis* infection that is not drug resistant include isoniazid, rifampin, ethambutol, streptomycin and pyrazinamide. "Second-line" chemotherapeutic agents used to treat a *Mycobacterium tuberculosis* infection that has demonstrated drug resistance to one or more "first-line" drugs include ofloxacin, ciprofloxacin, ethionamide, aminosalicylic acid, cycloserine, amikacin, kanamycin and capreomycin. In addition to the aforementioned, there are a number of new anti-tuberculosis therapeutic agents emerging from clinical studies that may also be employed as the one or more additional therapeutic agents in a combination with a compound of Formula I, IA, or IB including, but not limited to, TMC-207, OPC-67683, PA-824, LL-3858 and SQ-109.

Thus, the other antibiotic which may be combined with the compounds of Formula I, IA, IB or Formula II, IIA, IIB are for example rifampicin (rifampin); isoniazid; pyrazinamide; amikacin; ethionamide; moxifloxacin; ethambutol; streptomycin; para-aminosalicylic acid; cycloserine; capreomycin; kanamycin; thioacetazone; quinolones/fluoroquinolones such as for example ofloxacin, ciprofloxacin, sparfloxacin; macrolides such as for example clarithromycin, clofazimine, amoxicillin with clavulanic acid; rifamycins; rifabutin; rifapentine.

In a further aspect, the one or more additional therapeutic agent is, for example, an agent useful for the treatment of tuberculosis in a mammal, therapeutic vaccines, anti-bacterial agents, anti-viral agents; antibiotics and/or agents for the treatment of HIV/AIDS. Examples of such therapeutic agents include isoniazid (INH), ethambutol, rifampin, pirazinamide, streptomycin, capreomycin, ciprofloxacin and clofazimine.

In one aspect, the one or more additional therapeutic agent is a therapeutic vaccine. A compound of Formula I, IA, or IB or a pharmaceutically acceptable salt thereof, may thus be administered in conjunction with vaccination against mycobacterial infection, in particular vaccination against *Mycobacterium tuberculosis* infection. Existing vaccines against mycobacterial infection include *Bacillus* Calmette Guerin (BCG). Vaccines currently under development for the treatment, prophylaxis or amelioration of mycobacterial infection include: modified BCG strains which recombinantly express additional antigens, cytokines and other agents intended to improve efficacy or safety; attenuated mycobacteria which express a portfolio of antigens more similar to *Mycobacterium tuberculosis* than BCG; and subunit vaccines. Subunit vaccines may be administered in the form of one or more individual protein antigens, or a fusion or fusions of multiple protein antigens, either of which may optionally be adjuvanted, or in the form of a polynucleotide encoding one or more individual protein antigens, or encoding a fusion or fusions of multiple protein antigens, such as where the polynucleotide is administered in an expression vector. Examples of subunit vaccines include, but are not limited to: M72, a fusion protein derived from the antigens Mtb32a and Mtb39; HyVac-1, a fusion protein derived from antigen 85b and ESAT-6; HyVac-4, a fusion protein derived from antigen 85b and Tb10.4; MVA85a, a modified vaccinia virus Ankara expressing antigen 85a; and Aeras-402, adenovirus 35 expressing a fusion protein derived from antigen 85a, antigen 85b and Tb10.4.

Abbreviations employed herein include the following:

ACN=acetonitrile; CBZ-Cl=benzyl chloroformate; CDCl$_3$=deuterated chloroform; DCM=dichloromethane; DIAD=diisopropyl diazodicarboxylate, DIEA=N,N-Diisopropylethylamine; DMF=N,N-dimethylformamide; DMSO=dimethyl sulfoxide; Et=ethyl; EtOAc=ethyl acetate; EtOH=ethanol; GFP=green fluorescent protein; HATU=(1-[Bis(dimethylamino)methylene]-1H-1,2,3-triazolo[4,5-b]pyridinium 3-oxid hexafluorophosphate), HET=heterocycle; H$_2$=hydrogen gas, HPLC=high-performance liquid chromatography; LC-MS=liquid chromatography/mass spectrometry; Me=methyl; MeOH=methanol; MIC=minimum inhibitory concentration; MW=molecular weight; MS=mass spectrometry; Mtb=*Mycobacterium tuberculosis*; Pd—C=palladium on carbon; RT=room temperature; TB=tuberculosis; TEA=triethylamine; TFA=trifluoroacetic acid; THF=tetrahydrofuran; and TBDMS=tert-butyl dimethylsilyl.

Methods for Making the Compounds of Formula (I):

The compounds of Formula (I) can be prepared according to the following reaction schemes and EXAMPLES, or modifications thereof, using readily available starting materials, reagents and conventional synthesis procedures. In these reactions, it is also possible to make use of variations which are themselves known to those of ordinary skill in this art, but are not mentioned in greater detail. Alternative synthetic pathways and analogous structures will be apparent to those skilled in the art of organic synthesis in light of the following reaction schemes and EXAMPLES.

EXAMPLES

Example 1

Synthesis of (5R)-3-[2-fluoro-4'-(methylsulfonyl)biphenyl-4-yl]-5-(hydroxymethyl)-1,3-oxazolidin-2-one

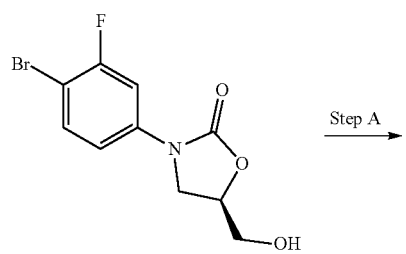

Step A →

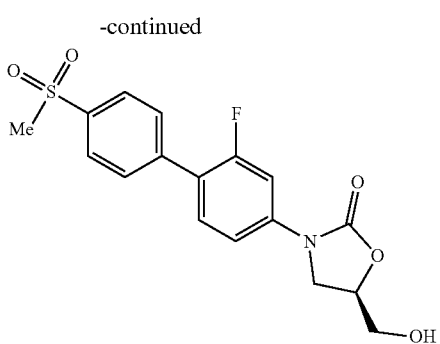

Step A: Synthesis of (5R)-3-[2-fluoro-4'-(methylsulfonyl)biphenyl-4-yl]-5-(hydroxymethyl)-1,3-oxazolidin-2-one (5R)-3-(4-bromo-3-fluorophenyl)-5-(hydroxymethyl)-1,3-oxazolidin-2-one (171.8 g, 592.2 mmol, 1 equiv), (4-methanesulfonylphenyl)boronic acid (130.4 g, 651.9 mmol, 1.10 equiv), potassium carbonate (163 g, 1179 mmol, 1.99 equiv), THF (1750 mL), water (580 mL), and [1,1'-Bis(diphenylphosphino)ferrocene]dichloropalladium(II) (Pd(dppf)Cl$_2$) (21.6 g, 29.52 mmol, 0.05 equiv) were placed into a 5-L 4-necked round-bottom flask, purged and maintained with an inert atmosphere of nitrogen. The reaction mixture was warmed to 70° C. and allowed to stir at that temperature for 16 h. The reaction mixture was cooled to ambient temperature, filtered, and the precipitate was collected. The precipitate was then dissolved in DMSO (1700 mL). Silica gel (27 g) was added, and the resulting mixture was warmed to 40° C. and allowed to stir at that temperature for 16 h. The mixture was filtered. Water (684 mL) was added to the filtrate, and the resulting mixture filtered. The solids were collected and dried under reduced pressure to afford the title compound. MS (ESI) m/z: 364.0 [M+H$^+$]; $^1$H NMR (400 MHz, DMSO-d$_6$): δ 8.03 (d, J=8.3 Hz, 2H), 7.87-7.80 (m, 2H), 7.73-7.63 (m, 2H), 7.52 (dd, J=8.6, 2.3 Hz, 1H), 5.27 (s, 1H), 4.77 (ddt, J=9.5, 6.4, 3.5 Hz, 1H), 4.16 (t, J=9.0 Hz, 1H), 3.90 (dd, J=9.0, 6.1 Hz, 1H), 3.71 (d, J=12.5 Hz, 1H), 3.59 (d, J=12.5 Hz, 1H), 3.28 (s, 3H).

Example 2

Synthesis of (5R)-3-[3,5-difluoro-4-(4-fluoro-1,1-dioxidotetrahydro-2H-thiopyran-4-yl)phenyl]-5-(hydroxymethyl)-1,3-oxazolidin-2-one

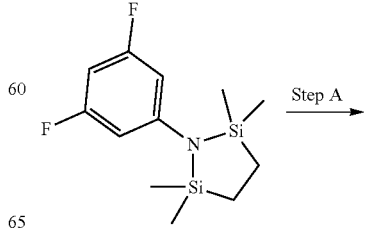

Step A →

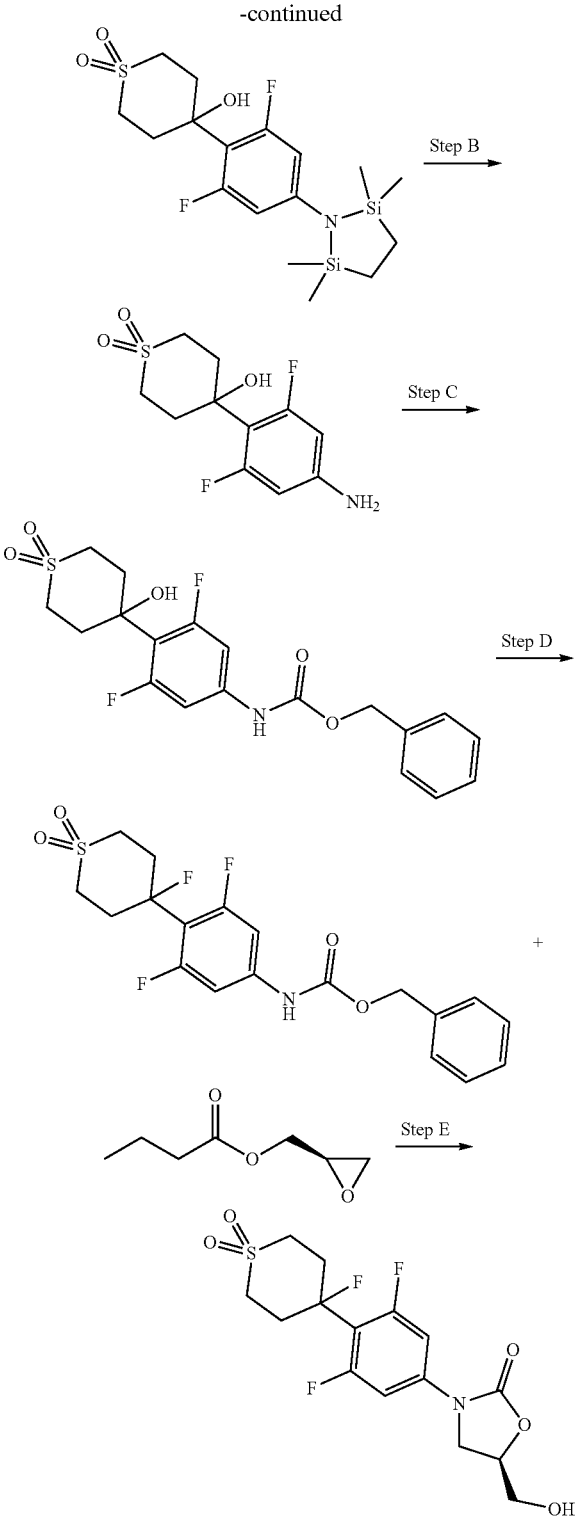

THF (120 mL) at −78° C. under nitrogen and the reaction mixture was allowed to stir for 2 h. Dihydro-2H-thiopyran-4(3H)-one 1,1-dioxide (6.88 g, 46.4 mmol) was added, and the reaction mixture was allowed to stir for 2 h. A saturated aqueous solution of ammonium chloride (300 mL) was added to the reaction mixture, and the resulting mixture was extracted with ethyl acetate (3×100 mL). The combined organic layers were dried over sodium sulfate. The mixture was filtered and the filtrate was concentrated under reduced pressure to afford the title compound in sufficient purity for use in the next step.

Step B: Synthesis of 4-(4-amino-2,6-difluorophenyl)tetrahydro-2H-thiopyran-4-ol 1,1-dioxide Potassium carbonate (6.59 g, 47.7 mmol) was added to a solution of 4-[2,6-difluoro-4-(2,2,5,5-tetramethyl-1,2,5-azadisilolidin-1-yl)phenyl]tetrahydro-2H-thiopyran-4-ol 1,1-dioxide (10 g) in methanol (100 mL) at ambient temperature, and the reaction mixture was allowed to stir for 3 h. Water (30 mL) was then added to the reaction mixture, and the resulting mixture was concentrated, under reduced pressure, to remove any methanol. The resulting mixture was filtered and the precipitate was washed with petroleum ether/ethyl acetate (2/1). The resulting solid was dried under reduced pressure to afford the title compound. $^1$H NMR (500 MHz, DMSO-$d_6$): δ 6.12 (d, J=13.5 Hz, 2H), 5.67 (s, 2H), 5.52 (br s, 1H), 3.37 (br d, J=2.5 Hz, 2H), 2.96 (br d, J=11.5 Hz, 2H), 2.48-2.44 (m, 2H), 2.28 (br d, J=13.0 Hz, 2H).

Step C: Synthesis of benzyl [3,5-difluoro-4-(4-hydroxy-1,1-dioxidotetrahydro-2H-thiopyran-4-yl)phenyl]carbamate N,N-dimethylaniline (6.29 g, 51.9 mmol) was added to a solution of 4-(4-amino-2,6-difluorophenyl)tetrahydro-2H-thiopyran-4-ol 1,1-dioxide (7.2 g, 26.0 mmol) in THF (80 mL) at 0° C., and the reaction mixture was allowed to stir for 20 min. Benzyl chloroformate (3.89 mL, 27.3 mmol) was added slowly, and the reaction mixture was allowed to slowly warm to ambient temperature and was stirred for 4 h. Water (40 mL) was then added to the reaction mixture, and the resulting mixture was extracted with ethyl acetate (3×30 mL). The organic layers were combined, dried over sodium sulfate. The resulting mixture was filtered, and the filtrate concentrated under reduced pressure. The resulting residue was washed with petroleum ether (4×20 mL). The resulting mixture was filtered, and the precipitate washed with ethyl acetate/petroleum ether (1/1; 2×10 mL). The resulting solid was dried under reduced pressure to afford the title compound in sufficient purity for use in the next step. MS (ESI) m/z: 394.1 [M−H$_2$O+H$^+$]. $^1$H NMR (DMSO-$d_6$, 400 MHz): δ 10.18 (s, 1H), 7.45-7.33 (m, 5H), 7.10 (d, J=12.8 Hz, 2H), 5.79 (br s, 1H), 5.15 (s, 2H), 3.39 (br s, 2H), 2.99 (br d, J=12.8 Hz, 2H), 2.59-2.51 (m, 2H), 2.33-2.25 (m, 2H).

Step D: Synthesis of benzyl [3,5-difluoro-4-(4-fluoro-1,1-dioxidotetrahydro-2H-thiopyran-4-yl)phenyl]carbamate Bis(2-methoxyethyl)aminosulfur trifluoride (5.75 mL, 31.2 mmol) was added to a solution of benzyl [3,5-difluoro-4-(4-hydroxy-1,1-dioxidotetrahydro-2H-thiopyran-4-yl)phenyl]carbamate (9.0 g, 20.8 mmol) in dichloromethane (60 mL) at 0° C., and the reaction mixture was allowed to warm to ambient temperature and stirred for 2 h. A saturated aqueous solution of sodium bicarbonate (40 mL) was added to the reaction mixture, and the resulting mixture was concentrated under reduced pressure to remove dichloromethane. The resulting mixture was filtered, and the Step A: Synthesis of 4-[2,6-difluoro-4-(2,2,5,5-tetramethyl-1,2,5-azadisilolidin-1-yl)phenyl]tetrahydro-2H-thiopyran-4-ol 1,1-dioxide Sec-Butyllithium (Sec-BuLi) (44.2 mL, 57.5 mmol) was added to a stirred solution of 1-(3,5-difluorophenyl)-2,2,5,5-tetramethyl-1,2,5-azadisilolidine (12 g, 44.2 mmol) in precipitate was washed with water (4×20 mL), petroleum ether (3×30 mL), and ethyl acetate (10 mL) sequentially. The resulting solid was dried under reduced pressure to afford the title compound. $^1$H NMR (DMSO-$d_6$, 400 MHz): δ 10.32 (s, 1H), 7.46-7.33 (m, 5H), 7.20 (d, J=12.8 Hz, 2H), 5.18 (s, 2H), 3.45-3.36 (m, 2H), 3.18 (br d, J=12.8 Hz, 2H), 2.80-2.60 (m, 4H).

Step E: Synthesis of (5R)-3-[3,5-difluoro-4-(4-fluoro-1,1-dioxidotetrahydro-2H-thiopyran-4-yl)phenyl]-5-(hydroxymethyl)-1,3-oxazolidin-2-one Lithium tert-butoxide (4.36 g, 54.4 mmol) was added to a solution of benzyl [3,5-difluoro-4-(4-fluoro-1,1-dioxidotetrahydro-2H-thiopyran-4-yl)phenyl]carbamate (7.5 g, 18.14 mmol) in THF (140 mL) at 0° C., and the reaction mixture allowed to stir for 20 min. (R)-oxiran-2-ylmethyl butyrate (3.92 g, 27.2 mmol) was then added, and the reaction mixture was warmed to ambient temperature and allowed to stir for 16 h. The reaction mixture was poured into a cold, saturated aqueous solution of ammonium chloride (400 mL) and the resulting mixture was concentrated under reduced pressure to remove THF. The resulting mixture was filtered, and the precipitate collected. The precipitate was purified by preparative HPLC, eluting with a gradient of acetonitrile:water containing 10 mM ammonium carbonate—20:80 to 50:50 to afford the title compound. MS (ESI) m/z: 380.0 [M+H$^+$]. $^1$H NMR (DMSO-$d_6$, 400 MHz): δ 7.39 (d, J=12.8 Hz, 2H), 5.23 (t, J=5.6 Hz, 1H), 4.79-4.71 (m, 1H), 4.07 (t, J=9.2 Hz, 1H), 3.83 (dd, J=9.2, 6.0 Hz, 1H), 3.71-3.64 (m, 1H), 3.58-3.51 (m, 1H), 3.47-3.38 (m, 2H), 3.19 (br d, J=12.0 Hz, 2H), 2.83-2.61 (m, 4H).

Example 3

Synthesis of {(5R)-3-[3,5-difluoro-4-(4-fluoro-1,1-dioxo-1λ$^6$-thian-4-yl)phenyl]-2-oxo-1,3-oxazolidin-5-yl}methyl dihydrogen phosphate

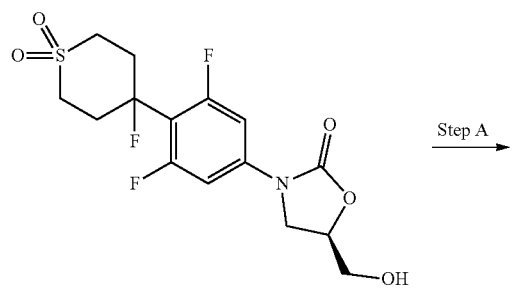

Step A

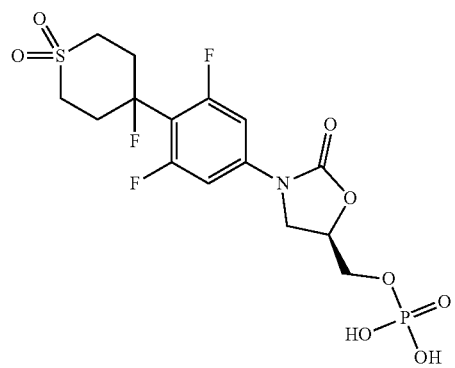 [SMILES: O=C1O[C@@H](COP(=O)(O)O)CN1c1cc(F)c(C2(F)CCS(=O)(=O)CC2)c(F)c1]

To a solution of (R)-3-(3,5-difluoro-4-(4-fluoro-1,1-dioxidotetrahydro-2H-thiopyran-4-yl)phenyl)-5-(hydroxymethyl)oxazolidin-2-one (500 mg, 1.32 mmol) in tetrahydrofuran (8 mL) at 0° C. was added triethylamine (0.551 mL, 3.95 mmol) followed by phosphorus(V) oxychloride (0.369 mL, 3.95 mmol) and the reaction mixture allowed to stir for 3 h. Water (20 mL) was added, and the resulting mixture concentrated under reduced pressure and the filtered. The precipitate was purified by preparative HPLC, eluting with a gradient of acetonitrile:water containing 0.05% HCl—15:85 to 35:65 to afford the title compound. MS (ESI) m/z: 460.2 [M+H$^+$]. $^1$H NMR (DMSO-$d_6$, 400 MHz): δ 7.38 (d, J=12.8 Hz, 2H), 4.93 (br s, 1H), 4.15 (t, J=9.6 Hz, 1H), 4.11-3.98 (m, 2H), 3.83 (dd, J=9.2, 6.0 Hz, 1H), 3.47-3.37 (m, 2H), 3.20 (br d, J=13.6 Hz, 2H), 2.83-2.63 (m, 4H).

The following compounds were made using the methods described in Example 1 or 2, substituting the appropriate reactants and/or reagents.

| Example | Structure | IUPAC Name | MS (M + H$^+$) |
|---|---|---|---|
| 4 | 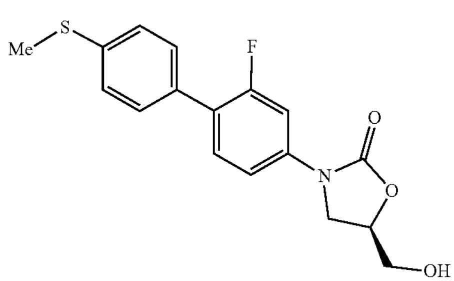 [SMILES: CSc1ccc(-c2ccc(N3C[C@H](CO)OC3=O)cc2F)cc1] | (5R)-3-[2-fluoro-4'-(methylsulfanyl)[1,1'-biphenyl]-4-yl]-5-(hydroxymethyl)-1,3-oxazolidin-2-one | 334.1 |

| Example | Structure | IUPAC Name | MS (M + H+) |
|---|---|---|---|
| 5 | 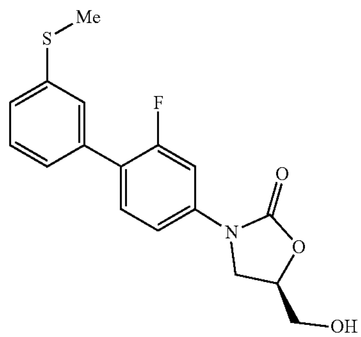 [SMILES: CSc1cccc(-c2ccc(N3C[C@H](CO)OC3=O)cc2F)c1] | (5R)-3-[2-fluoro-3'-(methylsulfanyl)[1,1'-biphenyl]-4-yl]-5-(hydroxymethyl)-1,3-oxazolidin-2-one | 334.1 |
| 6 | 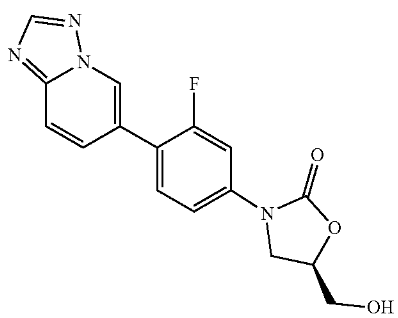 [SMILES: O=C1O[C@@H](CO)CN1c1ccc(-c2ccc3ncnn3c2)c(F)c1] | (5R)-3-[3-fluoro-4-([1,2,4]triazolo[1,5-a]pyridin-6-yl)phenyl]-5-(hydroxymethyl)-1,3-oxazolidin-2-one | 329.1 |
| 7 | 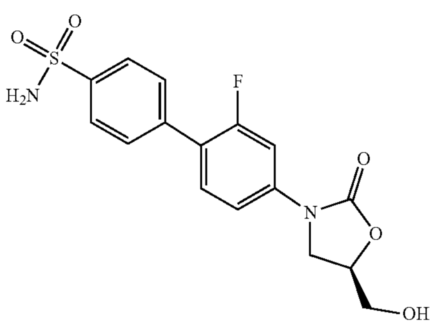 [SMILES: NS(=O)(=O)c1ccc(-c2ccc(N3C[C@H](CO)OC3=O)cc2F)cc1] | 2'-fluoro-4'-[(5R)-5-(hydroxymethyl)-2-oxo-1,3-oxazolidin-3-yl][1,1'-biphenyl]-4-sulfonamide | 367.1 |
| 8 | 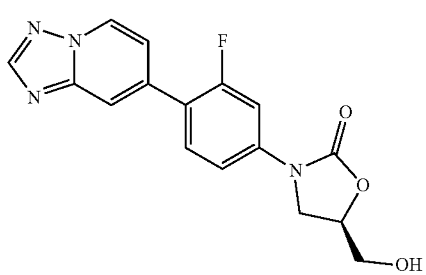 [SMILES: O=C1O[C@@H](CO)CN1c1ccc(-c2ccn3ncnc3c2)c(F)c1] | (5R)-3-[3-fluoro-4-([1,2,4]triazolo[1,5-a]pyridin-7-yl)phenyl]-5-(hydroxymethyl)-1,3-oxazolidin-2-one | 329.1 |
| 9 | 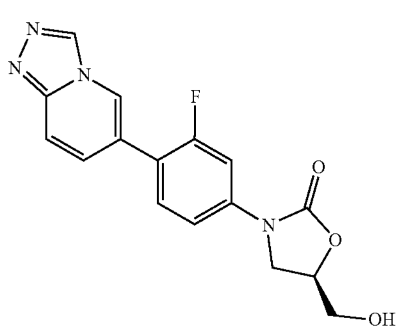 [SMILES: O=C1O[C@@H](CO)CN1c1ccc(-c2ccc3nncn3c2)c(F)c1] | (5R)-3-[3-fluoro-4-([1,2,4]triazolo[4,3-a]pyridin-6-yl)phenyl]-5-(hydroxymethyl)-1,3-oxazolidin-2-one | 329.1 |

-continued

| Example | Structure | IUPAC Name | MS (M + H⁺) |
|---|---|---|---|
| 10 | 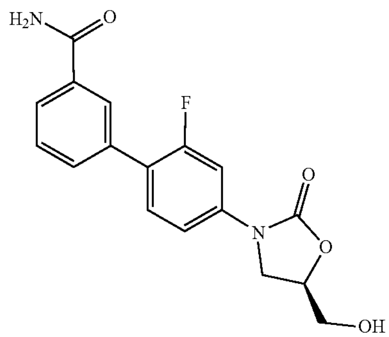 [SMILES: NC(=O)c1cccc(-c2ccc(N3C[C@H](CO)OC3=O)cc2F)c1] | 2'-fluoro-4'-[(5R)-5-(hydroxymethyl)-2-oxo-1,3-oxazolidin-3-yl][1,1'-biphenyl]-3-carboxamide | 331.1 |
| 11 | 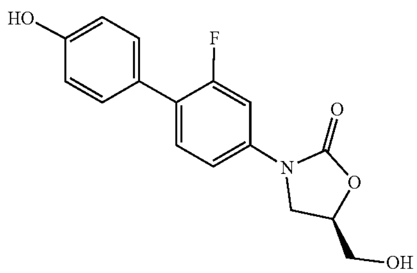 [SMILES: O=C1O[C@@H](CO)CN1c1ccc(-c2ccc(O)cc2)c(F)c1] | (5R)-3-(2-fluoro-4'-hydroxy[1,1'-biphenyl]-4-yl)-5-(hydroxymethyl)-1,3-oxazolidin-2-one | 304.1 |
| 12 | 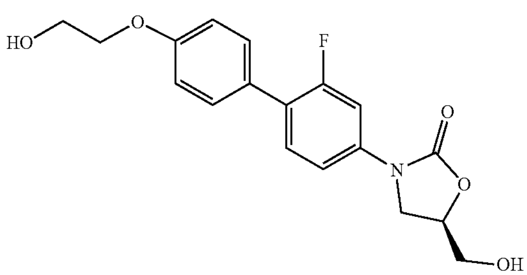 [SMILES: O=C1O[C@@H](CO)CN1c1ccc(-c2ccc(OCCO)cc2)c(F)c1] | (5R)-3-[2-fluoro-4'-(2-hydroxyethoxy)[1,1'-biphenyl]-4-yl]-5-(hydroxymethyl)-1,3-oxazolidin-2-one | 348.0 |
| 13 | 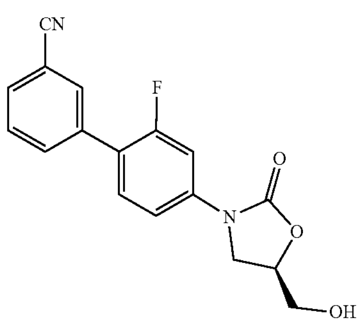 [SMILES: N#Cc1cccc(-c2ccc(N3C[C@H](CO)OC3=O)cc2F)c1] | 2'-fluoro-4'-[(5R)-5-(hydroxymethyl)-2-oxo-1,3-oxazolidin-3-yl][1,1'-biphenyl]-3-carbonitrile | 313.1 |
| 14 | 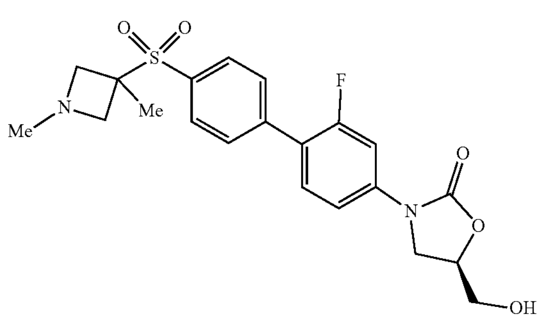 [SMILES: CN1CC(C)(S(=O)(=O)c2ccc(-c3ccc(N4C[C@H](CO)OC4=O)cc3F)cc2)C1] | (5R)-3-[4'-(1,3-dimethylazetidine-3-sulfonyl)-2-fluoro[1,1'-biphenyl]-4-yl]-5-(hydroxymethyl)-1,3-oxazolidin-2-one | 435.1 |

-continued

| Example | IUPAC Name | MS (M + H⁺) |
|---|---|---|
| 15 | 4-{2,6-difluoro-4-[(5R)-5-(hydroxymethyl)-2-oxo-1,3-oxazolidin-3-yl]phenyl}-3,6-dihydro-1λ6-thiopyran-1,1(2H)-dione | 359.9 |
| 16 | 4-{2,6-difluoro-4-[(5R)-5-(hydroxymethyl)-2-oxo-1,3-oxazolidin-3-yl]phenyl}-1,1-dioxo-1λ6-thiane-4-carbonitrile | 387.1 |
| 17 | 5-{2,6-difluoro-4-[(5R)-5-(hydroxymethyl)-2-oxo-1,3-oxazolidin-3-yl]phenyl}hexahydro-2λ6-thieno[3,4-c]pyrrole-2,2(1H)-dione | 389.0 |
| 18 | (5R)-3-[4-(5-acetyl-2,5-diazabicyclo[4.1.0]heptan-2-yl)-3,5-difluorophenyl]-5-(hydroxymethyl)-1,3-oxazolidin-2-one | 368.1 |
| 19 | (5R)-3-[3-fluoro-4-(3-methyl[1,2,4]triazolo[4,3-a]pyridin-7-yl)phenyl]-5-(hydroxymethyl)-1,3-oxazolidin-2-one | 343.0 |

-continued

| Example | Structure | IUPAC Name | MS (M + H⁺) |
|---|---|---|---|
| 20 | 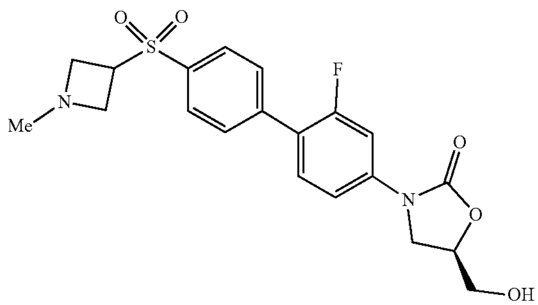 [SMILES: CN1CC(S(=O)(=O)c2ccc(-c3ccc(N4C[C@H](CO)OC4=O)cc3F)cc2)C1] | (5R)-3-[2-fluoro-4'-(1-methylazetidine-3-sulfonyl)[1,1'-biphenyl]-4-yl]-5-(hydroxymethyl)-1,3-oxazolidin-2-one | 421.0 |
| 21 | 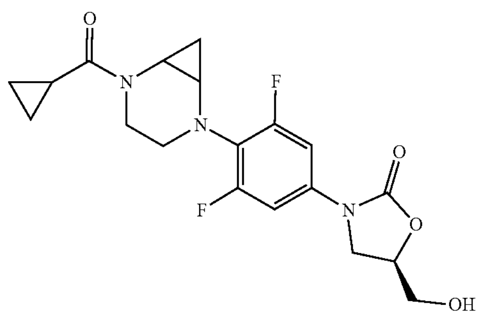 [SMILES: O=C1O[C@@H](CO)CN1c1cc(F)c(N2CCN(C(=O)C3CC3)C3CC32)c(F)c1] | (5R)-3-{4-[5-(cyclopropanecarbonyl)-2,5-diazabicyclo[4.1.0]heptan-2-yl]-3,5-difluorophenyl}-5-(hydroxymethyl)-1,3-oxazolidin-2-one | 394.1 |
| 22 | 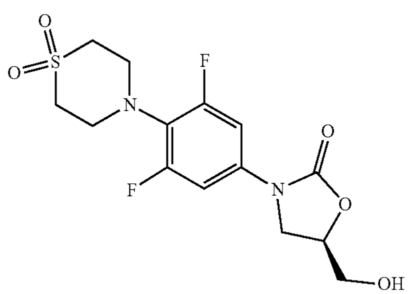 [SMILES: O=C1O[C@@H](CO)CN1c1cc(F)c(N2CCS(=O)(=O)CC2)c(F)c1] | 4-{2,6-difluoro-4-[(5R)-5-(hydroxymethyl)-2-oxo-1,3-oxazolidin-3-yl]phenyl}-1$\lambda^6$-thiomorpholine-1,1-dione | 363.0 |
| 23 | 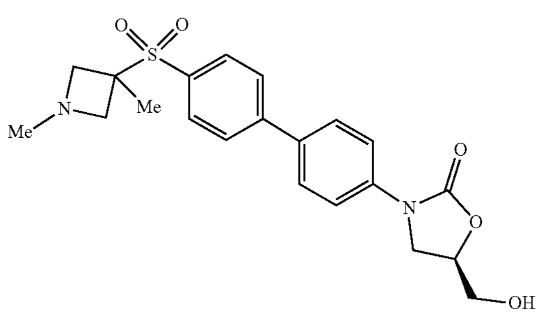 [SMILES: CN1CC(C)(S(=O)(=O)c2ccc(-c3ccc(N4C[C@H](CO)OC4=O)cc3)cc2)C1] | (5R)-3-[4'-(1,3-dimethylazetidine-3-sulfonyl)[1,1'-biphenyl]-4-yl]-5-(hydroxymethyl)-1,3-oxazolidin-2-one | 417.2 |
| 24 | 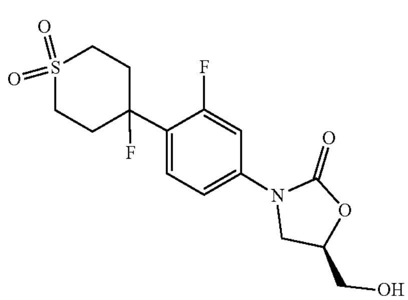 [SMILES: O=C1O[C@@H](CO)CN1c1ccc(C2(F)CCS(=O)(=O)CC2)c(F)c1] | 4-fluoro-4-[2-fluoro-4-[(5R)-5-(hydroxymethyl)-2-oxo-1,3-oxazolidin-3-yl]phenyl}-1$\lambda^6$-thiane-1,1-dione | 362.1 |

-continued

| Example | Structure | IUPAC Name | MS (M + H+) |
|---|---|---|---|
| 25 | 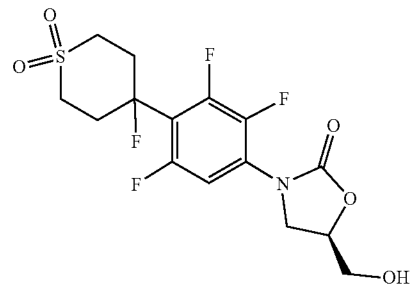 [SMILES: O=C1O[C@@H](CO)CN1c1cc(F)c(C2(F)CCS(=O)(=O)CC2)c(F)c1F] | 4-fluoro-4-{2,3,6-trifluoro-4-[(5R)-5-(hydroxymethyl)-2-oxo-1,3-oxazolidin-3-yl]phenyl}-1$\lambda^6$-thiane-1,1-dione | 398.1 |
| 26 | 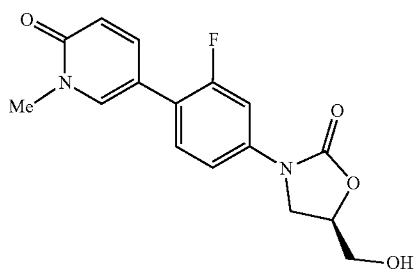 [SMILES: Cn1cc(-c2ccc(N3C[C@H](CO)OC3=O)cc2F)ccc1=O] | 5-{2-fluoro-4-[(5R)-5-(hydroxymethyl)-2-oxo-1,3-oxazolidin-3-yl]phenyl}-1-methylpyridin-2(1H)-one | 319.0 |
| 27 | 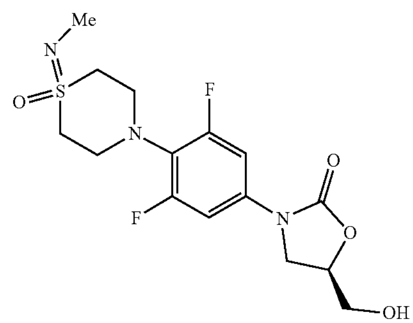 [SMILES: CN=S1(=O)CCN(c2c(F)cc(N3C[C@H](CO)OC3=O)cc2F)CC1] | 4-{2,6-difluoro-4-[(5R)-5-(hydroxymethyl)-2-oxo-1,3-oxazolidin-3-yl]phenyl}-1-(methylimino)-1$\lambda^6$-thiomorpholin-1-one | 376.0 |
| 28 | 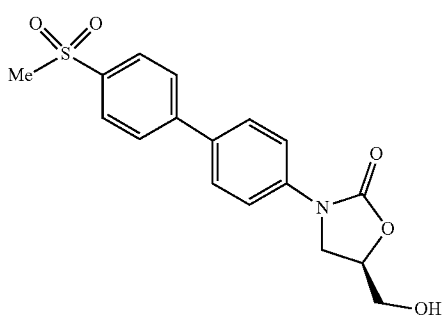 [SMILES: CS(=O)(=O)c1ccc(-c2ccc(N3C[C@H](CO)OC3=O)cc2)cc1] | (5R)-5-(hydroxymethyl)-3-[4'-(methanesulfonyl)[1,1'-biphenyl]-4-yl]-1,3-oxazolidin-2-one | 348.0 |
| 29 | 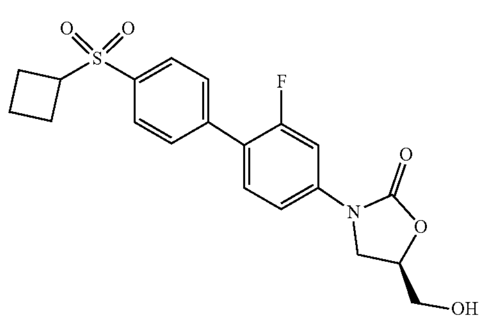 [SMILES: O=C1O[C@@H](CO)CN1c1ccc(-c2ccc(S(=O)(=O)C3CCC3)cc2)c(F)c1] | (5R)-3-[4'-(cyclobutanesulfonyl)-2-fluoro[1,1'-biphenyl]-4-yl]-5-(hydroxymethyl)-1,3-oxazolidin-2-one | 406.1 |

-continued

| Example | Structure | IUPAC Name | MS (M + H⁺) |
|---|---|---|---|
| 30 | 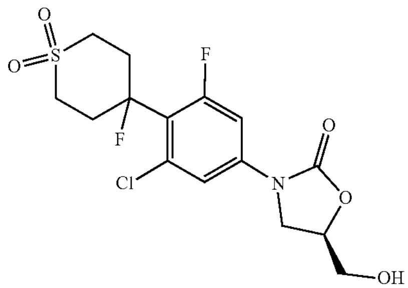 [SMILES: O=C1O[C@@H](CO)CN1c1cc(F)c(C2(F)CCS(=O)(=O)CC2)c(Cl)c1] | 4-{2-chloro-6-fluoro-4-[(5R)-5-(hydroxymethyl)-2-oxo-1,3-oxazolidin-3-yl]phenyl}-4-fluoro-1$\lambda^6$-thiane-1,1-dione | 396.0 |
| 31 | 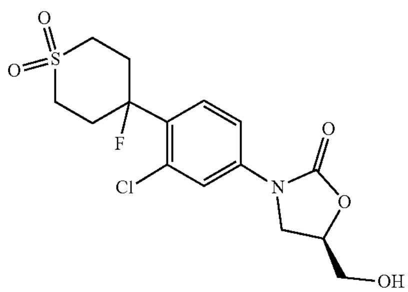 [SMILES: O=C1O[C@@H](CO)CN1c1ccc(C2(F)CCS(=O)(=O)CC2)c(Cl)c1] | 4-{2-chloro-4-[(5R)-5-(hydroxymethyl)-2-oxo-1,3-oxazolidin-3-yl]phenyl}-4-fluoro-1$\lambda^6$-thiane-1,1-dione | 378.0 |
| 32 | 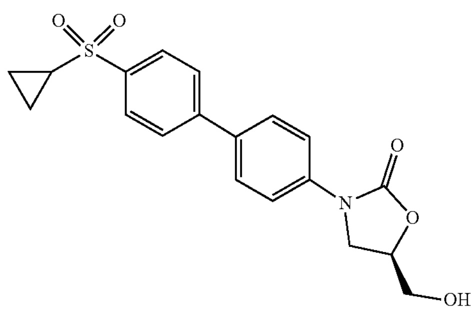 [SMILES: O=C1O[C@@H](CO)CN1c1ccc(-c2ccc(S(=O)(=O)C3CC3)cc2)cc1] | (5R)-3-[4'-(cyclopropanesulfonyl)[1,1'-biphenyl]-4-yl]-5-(hydroxymethyl)-1,3-oxazolidin-2-one | 374.1 |
| 33 | 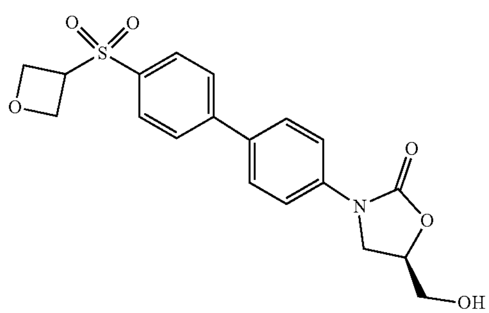 [SMILES: O=C1O[C@@H](CO)CN1c1ccc(-c2ccc(S(=O)(=O)C3COC3)cc2)cc1] | (5R)-5-(hydroxymethyl)-3-[4'-(oxetane-3-sulfonyl)[1,1'-biphenyl]-4-yl]-1,3-oxazolidin-2-one | 389.9 |
| 34 | 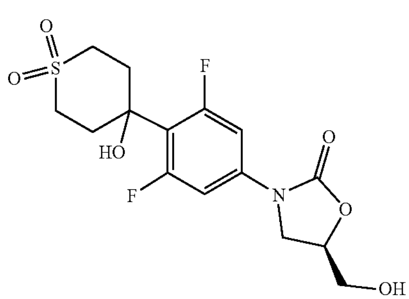 | 4-{2,6-difluoro-4-[(5R)-5-(hydroxymethyl)-2-oxo-1,3-oxazolidin-3-yl]phenyl}-4-hydroxy-1$\lambda^6$-thiane-1,1-dione | 360.0 |

-continued

| Example | Structure | IUPAC Name | MS (M + H⁺) |
|---|---|---|---|
| 35 | 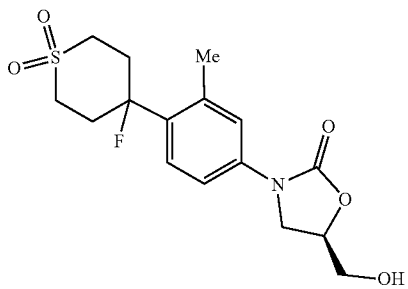 [SMILES: Cc1cc(N2C[C@H](CO)OC2=O)ccc1C1(F)CCS(=O)(=O)CC1] | 4-fluoro-4-{4-[(5R)-5-(hydroxymethyl)-2-oxo-1,3-oxazolidin-3-yl]-2-methylphenyl}-1$\lambda^6$-thiane-1,1-dione | 358.1 |
| 36 | 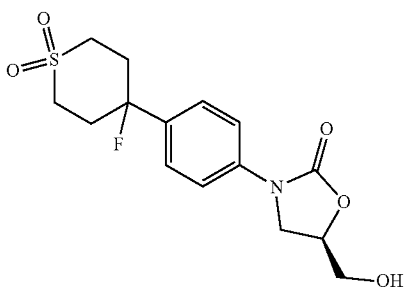 [SMILES: O=C1O[C@@H](CO)CN1c1ccc(C2(F)CCS(=O)(=O)CC2)cc1] | 4-fluoro-4-{4-[(5R)-5-(hydroxymethyl)-2-oxo-1,3-oxazolidin-3-yl]phenyl}-1$\lambda^6$-thiane-1,1-dione | 344.1 |
| 37 | 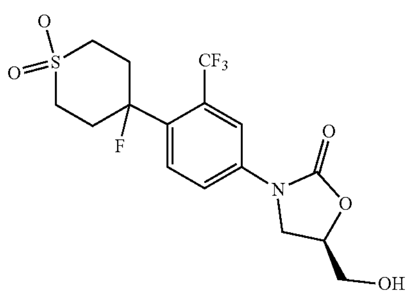 | 4-fluoro-4-{4-[(5R)-5-(hydroxymethyl)-2-oxo-1,3-oxazolidin-3-yl]-2-(trifluoromethyl)phenyl}-1$\lambda^6$-thiane-1,1-dione | 412.1 |
| 38 | 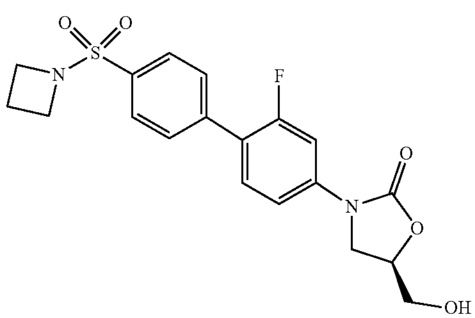 [SMILES: O=C1O[C@@H](CO)CN1c1ccc(-c2ccc(S(=O)(=O)N3CCC3)cc2)c(F)c1] | (5R)-3-[4'-(azetidine-1-sulfonyl)-2-fluoro[1,1'-biphenyl]-4-yl]-5-(hydroxymethyl)-1,3-oxazolidin-2-one | 407.0 |
| 39 | 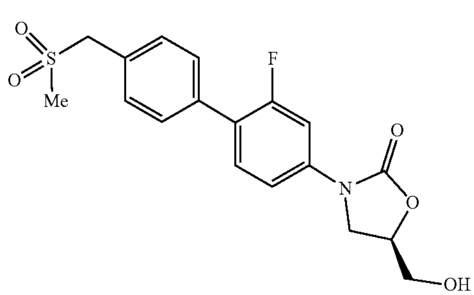 [SMILES: CS(=O)(=O)Cc1ccc(-c2ccc(N3C[C@H](CO)OC3=O)cc2F)cc1] | (5R)-3-{2-fluoro-4'-(methanesulfonyl)methyl][1,1'-biphenyl]-4-yl}-5-(hydroxymethyl)-1,3-oxazolidin-2-one | 380.1 |

| Example | Structure | IUPAC Name | MS (M + H+) |
|---|---|---|---|
| 40 | 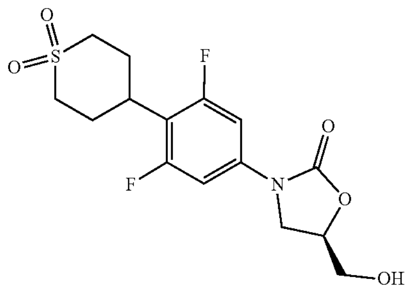 | 4-{2,6-difluoro-4-[(5R)-5-(hydroxymethyl)-2-oxo-1,3-oxazolidin-3-yl]phenyl}-1λ6-thiane-1,1-dione | 362.1 |
| 41 | 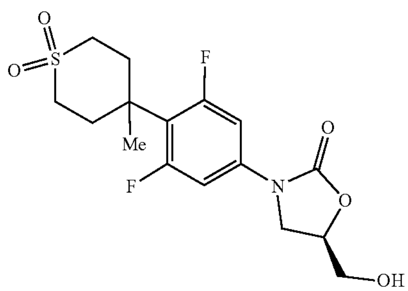 [SMILES: CC1(c2c(F)cc(N3C[C@H](CO)OC3=O)cc2F)CCS(=O)(=O)CC1] | 4-{2,6-difluoro-4-[(5R)-5-(hydroxymethyl)-2-oxo-1,3-oxazolidin-3-yl]phenyl}-4-methyl-1λ6-thiane-1,1-dione | 376.1 |

BIOLOGICAL ASSAYS

Biological Assays

*Mycobacterium tuberculosis* (Mtb) Growth Assay

Inhibition of *Mycobacterium tuberculosis* (Mtb) growth was assessed on two in vivo-relevant carbon sources, glucose and cholesterol, at pH 6.8. For glucose as a carbon source, the media consisted of Middlebrook 7H9 broth supplemented with 4 g/L glucose, 0.08 g/L NaCl, 5 g/L BSA fraction V and 0.05% tyloxapol. For cholesterol as a carbon source, the media consisted of Middlebrook 7H9 broth supplemented with 97 mg/L cholesterol, 0.08 g/L NaCl, 5 g/L BSA fraction V and 0.05% tyloxapol. Mtb expressing green fluorescent protein (Mtb-GFP; H37Rv pMSP12::GFP) was pre-adapted to growth on the relevant carbon source in Middlebrook 7H9-broth base supplemented with bovine serum albumin and tyloxapol prior to the screen. Bacteria were dispensed into 384-well microtiter plates at approximately $2\times10^4$ actively growing cells in 24 μL volumes per well. Microtiter plates were pre-dispensed with 0.2 μL compound, dimethylsulfoxide (negative control) or rifampicin (25 μM; positive control). Cells were exposed to 2-fold serial dilutions of compounds from 50 μM to 0.049 μM. In some experiments, compounds were tested at lower concentrations. Growth inhibition was assessed after a 7-day growth period by measuring fluorescence using a spectrophotometer. In negative control wells, cells were still actively growing at the time of readout. The lowest concentration of test compound required to inhibit 95% of the growth of the bacteria was defined as the MITC95. All studies were done in a BSL3 facility.

Mitochondrial Protein Synthesis Assay

Inhibition of mitochondrial protein synthesis was assessed in HepG2 cells by comparing the levels of two subunits of oxidative phosphorylation enzyme complexes, subunit I of Complex IV (COX-I) and the 70 kDa subunit of Complex II (SDH-A). COX-I is mitochondrial DNA encoded and SDH-A is nuclear DNA encoded. HepG2 cells were seeded in 96-well collagen coated plates at 8,000 cells per well and exposed to 2-fold serial dilutions of compounds from 100 μM to 6.25 μM. Microtiter plates were incubated for approximately 5 replication cycles (4 days) prior to assessment of protein levels using a kit as described by the manufacturer (ab110217 MitoBiogenesis In Cell ELISA Kit, Abcam, Cambridge, MA). Inhibition of mitochondrial protein synthesis was expressed as a ratio of COX-1 to SDH-A levels and a ratio of COX-1 to total viable cell amount (determined by Janus Green (JG) staining).

| Example | Mtb Cho MITC95_μM | Mtb Glu MITC95_μM | MPS IC50_μM |
|---|---|---|---|
| 1 | 1.2 | 1.0 | 7 |
| 2 | 2.2 | 1.9 | >100 |
| 4 | 0.24 | 0.21 | >100 |
| 7 | 0.96 | 0.77 | 1.7 |
| 8 | 1.8 | 1.5 | 3.7 |
| 12 | 0.39 | 0.78 | 19 |
| 14 | 0.78 | 0.78 | 23 |
| 15 | 1.6 | 1.6 | >100 |
| 16 | 1.6 | 1.6 | 50 |
| 17 | 3.1 | 2.3 | >100 |
| 18 | 3.1 | 3.1 | >100 |
| 19 | 1.2 | 1.2 | 18 |
| 20 | 0.39 | 0.39 | 7.4 |
| 21 | 3.1 | 6.3 | >13 |
| 22 | 6.3 | 3.9 | >100 |
| 23 | 3.1 | 1.6 | >100 |
| 24 | 6.3 | 6.3 | >50 |
| 25 | 6.3 | 6.3 | >100 |
| 26 | 6.3 | 6.3 | 28 |
| 27 | 6.3 | 6.3 | >100 |
| 28 | 1.6 | 1.6 | 32 |
| 29 | 3.1 | 3.1 | >100 |
| 30 | 13 | 6.3 | >100 |
| 31 | 13 | 13 | >100 |
| 32 | 3.1 | 3.1 | 30 |
| 33 | 2.3 | 3.1 | 9.7 |
| 34 | 25 | 25 | >100 |

-continued
| Example | Mtb Cho MITC95_μM | Mtb Glu MITC95_μM | MPS IC50_μM |
|---------|-------------------|-------------------|-------------|
| 35 | 50 | 25 | >100 |
| 36 | 38 | 50 | >50 |
| 37 | 50 | 50 | >100 |
| 38 | 6.3 | 6.3 | >13 |
| 39 | 1.2 | 1.6 | 1.5 |
| 41 | 9.4 | 6.3 | >100 |
| linezolid | 3.14 | 4.58 | 8 |
What is claimed:
1. A compound, or a pharmaceutically acceptable salt thereof, of formula IB:
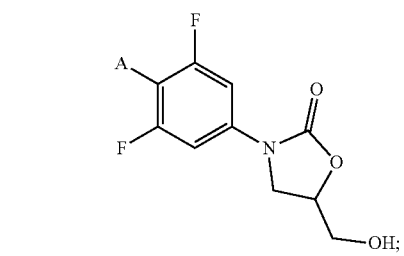
wherein A is
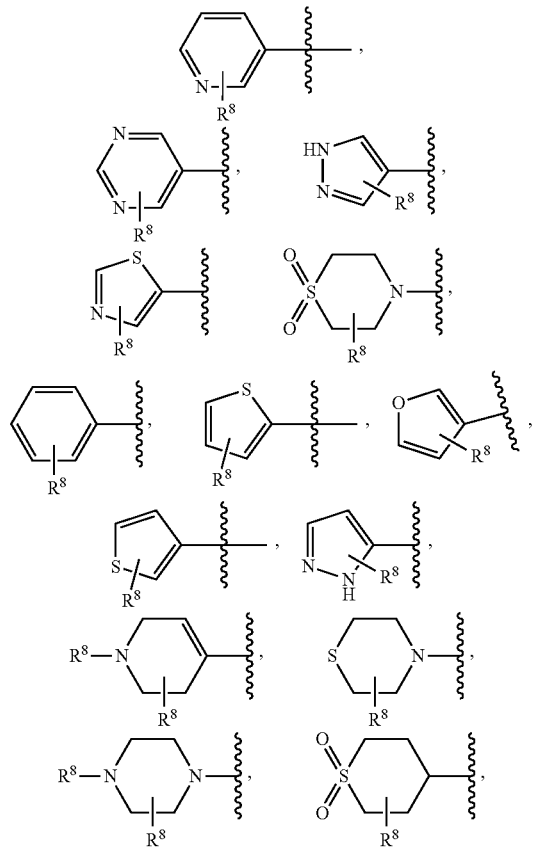
-continued
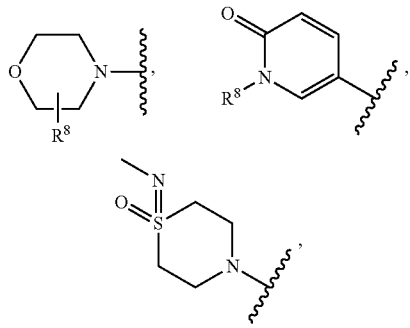
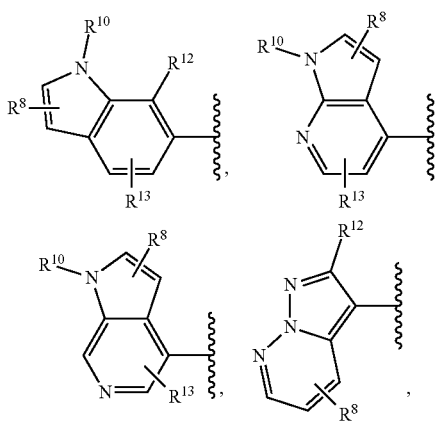

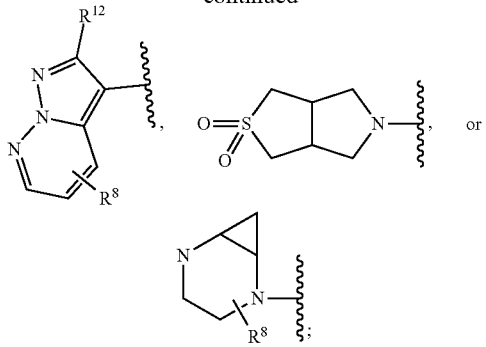

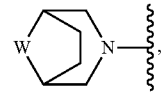

then W is selected from S, SO, SO$_2$, and S(=O)(=NH); and wherein --- represents a double or a single bond.

2. The compound of claim 1, or a pharmaceutically acceptable salt thereof, wherein A is:

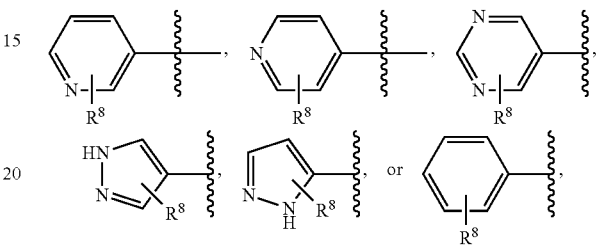

and wherein R$^8$ is halogen or SO$_2$CH$_3$.

3. The compound of claim 1, or a pharmaceutically acceptable salt thereof, wherein A is:

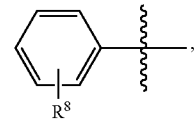

and wherein R$^8$ is halogen or SO$_2$CH$_3$.

4. The compound of claim 1, or a pharmaceutically acceptable salt thereof, wherein A is:

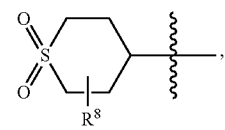

and wherein R$^8$ is halogen or SO$_2$CH$_3$.

5. The compound of claim 1, or a pharmaceutically acceptable salt thereof, wherein R$^8$ is halogen.

6. A compound, or a pharmaceutically acceptable salt thereof, which is:

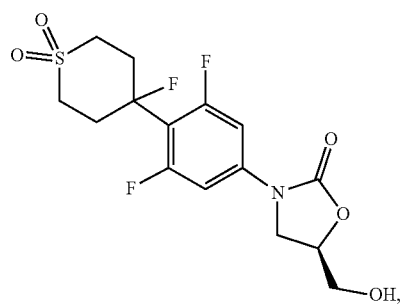

R$^8$ is halogen or SO$_2$CH$_3$;

each occurrence of R$^2$ is independently selected from H, C$_1$-C$_6$alkyl, C$_2$-C$_6$alkenyl, and C$_3$-C$_6$ cycloalkyl, wherein said C$_1$-C$_6$alkyl, said C$_2$-C$_6$alkenyl, and said C$_3$-C$_6$cycloalkyl are optionally substituted with up to four substituents, which are independently selected from halogen, —OCH$_3$, —OH, —NH$_2$, —NHCH$_3$, and —N(CH$_3$)$_2$;

R$^3$ is H, C$_1$-C$_6$alkyl, C$_2$-C$_6$alkenyl, C$_3$-C$_6$heterocycloalkyl and C$_3$-C$_6$cycloalkyl, wherein said C$_1$-C$_6$ alkyl, said C$_2$-C$_6$alkenyl, said C$_3$-C$_6$heterocycloalkyl and said C$_3$-C$_6$cycloalkyl are optionally substituted with up to four substituents, which are independently selected from halogen, methyl, —OCH$_3$, —OH, —NH$_2$, —NHCH$_3$, and —N(CH$_3$)$_2$; and each occurrence of R$^9$ is independently selected from H, C$_1$-C$_6$alkyl, and C$_3$-C$_6$ cycloalkyl m=is 0, 1, 2, or 3;

R$^{10}$ is selected from H, C$_1$-C$_6$alkyl and C$_3$-C$_6$cycloalkyl, wherein said C$_1$-C$_6$alkyl and said C$_3$-C$_6$ cycloalkyl are optionally substituted with from one to four substituents, which are independently selected from F, —OCH$_3$, —OH, NH$_2$, NHCH$_3$, and N(CH$_3$)$_2$;

R$^{11}$ is selected from H, C$_1$-C$_6$alkyl and C$_3$-C$_6$cycloalkyl, —COR$^9$, —COOR$^9$, —CON(R$^9$)$_2$, and —SO$_2$R$^9$;

each occurrence of R$^{12}$ is independently selected from H, halogen, C$_1$-C$_6$alkyl, C$_3$-C$_6$cycloalkyl, benzyl, —OCF$_3$, —OCHF$_2$, —OR$^3$, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, and —C(R$^9$)$_2$N(R$^2$)$_2$, wherein said C$_1$-C$_6$ alkyl, C$_3$-C$_6$cycloalkyl, and benzyl are optionally substituted with up to four substituents independently selected from F, —OCH$_3$, —OH, NH$_2$, NHCH$_3$, and N(CH$_3$)$_2$;

R$^{13}$ is selected from H, halogen, C$_1$-C$_6$alkyl, C$_3$-C$_6$cycloalkyl, benzyl, —OCF$_3$, —OCHF$_2$, —OR$^3$, —CN, —NO$_2$, —SR$^3$, —SF$_5$, —SCF$_3$, —SOR$^3$, —SO$_2$R$^3$, —S(=O)(=N)R$^2$, —N(R$^2$)$_2$, —NR$^2$COR$^3$, —SO$_2$N(R$^2$)$_2$, —NR$^2$SO$_2$R$^3$, —COOH, —COR$^9$, —COOR$^3$, —CON(R$^2$)$_2$, and —C(R$^9$)$_2$N(R$^2$)$_2$, wherein said C$_1$-C$_6$ alkyl, C$_3$-C$_6$cycloalkyl, and benzyl are optionally substituted with up to four substituents independently selected from F, —OCH$_3$, —OH, NH$_2$, NHCH$_3$, and N(CH$_3$)$_2$; and W is selected from O, S, SO, SO$_2$, and S(=O)(=NH), wherein when A is 67
-continued
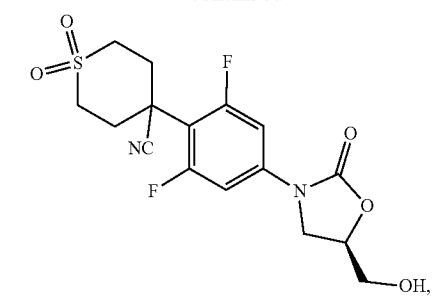
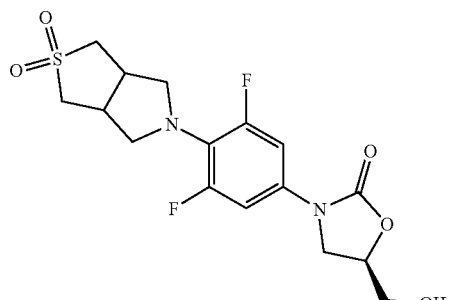
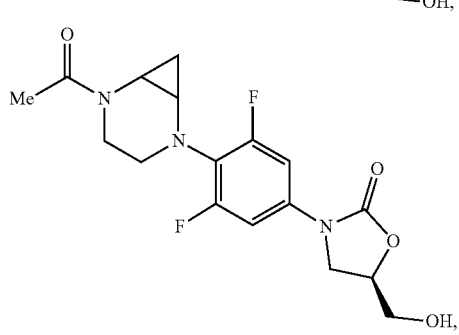
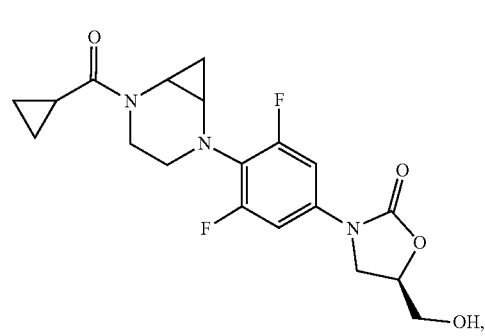
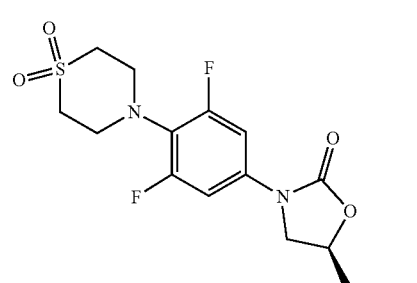
68
-continued
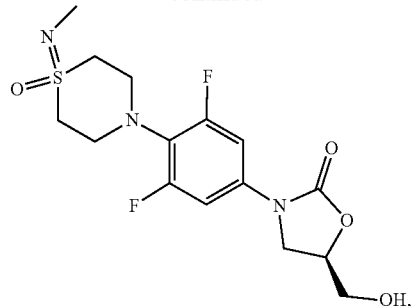
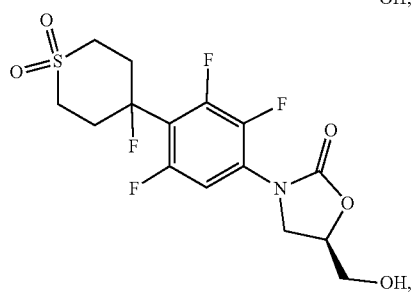
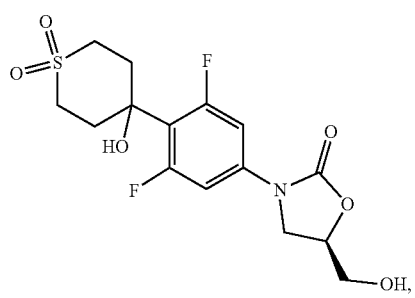
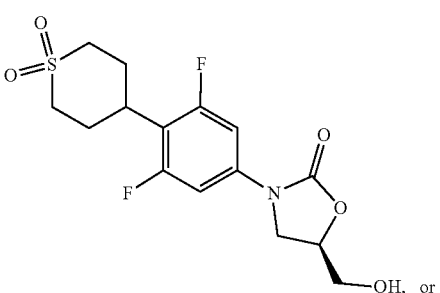
7. The compound of claim 6, or a pharmaceutically acceptable salt thereof, which is:

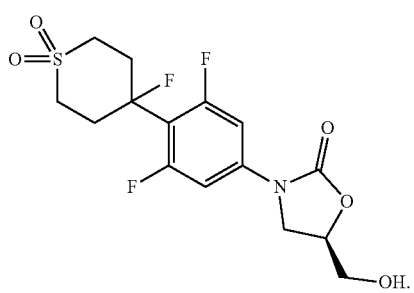 [SMILES: O=C1O[C@@H](CO)CN1c1cc(F)c(C2(F)CCS(=O)(=O)CC2)c(F)c1]

8. A pharmaceutical composition which comprises a therapeutically effective amount of a compound according to claim 1, or a pharmaceutically acceptable salt thereof, and a pharmaceutically acceptable carrier.

9. A method for treating a bacterial infection which comprises administering to a subject in need of such treatment a therapeutically effective amount of a compound according to claim 1, or a pharmaceutically acceptable salt thereof.

10. The method of claim 9, wherein the bacterial infection is due to *Mycobacterium tuberculosis*.

11. The method according to claim 10, further comprising the step of administering a second therapeutic agent for treating *Mycobacterium tuberculosis*.

12. The method of claim 11, wherein the second therapeutic agent is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terididone, para-aminosalicylic acid, clofazimine, clarithromycin, amoxicillin-clavulanate, thiacetazone, meropenem-clavulanate, and thioridazine.

13. A pharmaceutical composition which comprises a therapeutically effective amount of a compound according to claim 6, or a pharmaceutically acceptable salt thereof, and a pharmaceutically acceptable carrier.

14. A method for treating a bacterial infection which comprises administering to a subject in need of such treatment a therapeutically effective amount of a compound according to claim 6, or a pharmaceutically acceptable salt thereof.

15. The method of claim 14, wherein the bacterial infection is due to *Mycobacterium tuberculosis*.

16. The method according to claim 15, further comprising the step of administering a second therapeutic agent for treating *Mycobacterium tuberculosis*.

17. The method of claim 16, wherein the second therapeutic agent is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terididone, para-aminosalicylic acid, clofazimine, clarithromycin, amoxicillin-clavulanate, thiacetazone, meropenem-clavulanate, and thioridazine.

* * * * *